(12) United States Patent
Kim et al.

(10) Patent No.: US 8,343,640 B2
(45) Date of Patent: Jan. 1, 2013

(54) MATERIAL FOR ORGANIC PHOTOELECTRIC DEVICE, AND ORGANIC PHOTOELECTRIC DEVICE INCLUDING THE SAME

(75) Inventors: Nam-Soo Kim, Bucheon-si (KR); Eun-Sun Yu, Gyeonggi-do (KR); Young-Hoon Kim, Anyang-si (KR); Mi-Young Chae, Yongin-si (KR)

(73) Assignee: Cheil Industries, Inc., Gumi-Si, Kyeongsangbuk-do (KR)

( * ) Notice: Subject to any disclaimer, the term of this patent is extended or adjusted under 35 U.S.C. 154(b) by 211 days.

(21) Appl. No.: 12/659,356

(22) Filed: Mar. 5, 2010

(65) Prior Publication Data

US 2010/0163857 A1 Jul. 1, 2010

Related U.S. Application Data

(63) Continuation of application No. PCT/KR2008/005263, filed on Sep. 5, 2008.

(30) Foreign Application Priority Data

Sep. 5, 2007 (KR) .................. 10-2007-0090015

(51) Int. Cl.
  *H01L 51/54* (2006.01)
  *C09K 11/06* (2006.01)
(52) U.S. Cl. ........ 428/690; 428/917; 313/504; 313/506; 257/40; 257/102; 257/103; 257/E51.05; 257/E51.051; 252/301.16; 544/242
(58) Field of Classification Search .............. 548/440
See application file for complete search history.

(56) References Cited

U.S. PATENT DOCUMENTS

| | | | |
|---|---|---|---|
| 2004/0086745 A1 * | 5/2004 | Iwakuma et al. | ............. 428/690 |
| 2007/0190355 A1 | 8/2007 | Ikeda et al. | |
| 2007/0257600 A1 | 11/2007 | Matsuura et al. | |

FOREIGN PATENT DOCUMENTS

| | | |
|---|---|---|
| CN | 1918947 A | 2/2007 |
| EP | 1 718 121 A1 | 11/2006 |
| JP | 2003-022893 A | 1/2003 |
| JP | 2004-022334 A | 1/2004 |
| WO | WO 2005-085387 A1 | 9/2005 |

OTHER PUBLICATIONS

Baldo, M.A., et al., "Very High-Efficiency Green Organic Light-Emitting Devices Based on Electrophosphorescence", Applied Physics Letters, 75(1):4-6 (Jul. 5, 1999).
O'Brien, D.F., et al., "Improved Energy Transfer in Electrophosphorescent Devices," Applied Physics Letters, 74(3):442-444 (Jan. 18, 1999).
Tang, C.W., et al., "Organic electroluminescent diodes", Applied Physics Letters, 51(12):913-915 (1987).

* cited by examiner

*Primary Examiner* — Jennifer Chriss
*Assistant Examiner* — Michael H Wilson
(74) *Attorney, Agent, or Firm* — Lee & Morse, P.C.

(57) ABSTRACT

A material for an organic photoelectric device includes a compound represented by the following Formula 1:

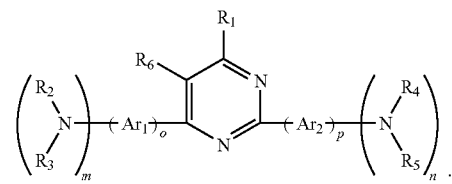

[Formula 1]

15 Claims, 2 Drawing Sheets

MATERIAL FOR ORGANIC PHOTOELECTRIC DEVICE, AND ORGANIC PHOTOELECTRIC DEVICE INCLUDING THE SAME

CROSS-REFERENCE TO RELATED APPLICATION

This application is a continuation of pending International Application No. PCT/KR2008/005263, entitled "Material for Organic Photoelectric Device and Organic Photoelectric Device Including the Same," which was filed on Sep. 5, 2008, the entire contents of which are hereby incorporated by reference.

BACKGROUND

1. Field

Embodiments relate to a material for an organic photoelectric device, and an organic photoelectric device including the same.

2. Description of the Related Art

A photoelectric device is, in a broad sense, a device for transforming photo energy to electrical energy, and conversely, for transforming electrical energy to photo energy. The photoelectric device may be exemplified by an organic light emitting diode, a solar cell, a transistor, and so on.

Particularly, among these photoelectric devices, the organic light emitting device employing organic light emitting diodes (OLED) has recently drawn attention due to the increase in demand for flat panel displays.

The organic light emitting device transforms electrical energy into light by applying current to an organic light emitting material. It has a structure in which a functional organic material layer is interposed between an anode and a cathode.

The organic light emitting diode has similar electrical characteristics to those of light emitting diodes (LEDs) in which holes are injected from an anode and electrons are injected from a cathode, then the holes and electrons move to opposite electrodes and are recombined to form excitons having high energy. The formed excitons generate light having a certain wavelength while shifting to a ground state.

In 1987, Eastman Kodak, Inc., developed an organic light emitting diode including a low molecular weight aromatic diamine and an aluminum complex as an emission-layer-forming material (Applied Physics Letters. 51, 913, 1987). C. W. Tang et al. disclosed a practicable device as an organic light emitting diode in 1987 (Applied Physics Letters, 51 12, 913-915, 1987).

The organic layer may have a structure in which a thin film (hole transport layer (HTL)) of a diamine derivative and a thin film of tris(8-hydroxy-quinolate)aluminum ($Alq_3$) are laminated. The $Alq_3$ thin film of $Alq_3$ functions an emission layer for transporting electrons.

Generally, the organic light emitting diode is composed of an anode of a transparent electrode, an organic thin layer of a light emitting region, and a metal electrode (cathode) formed on a glass substrate, in that order. The organic thin layer may include an emission layer, a hole injection layer (HIL), a hole transport layer (HTL), an electron transport layer (ETL), or an electron injection layer (EIL). It may further include an electron blocking layer or a hole blocking layer according to the emission characteristics of the emission layer.

When an electric field is applied to the organic light emitting diode, the holes and electrons are injected from the anode and the cathode, respectively. The injected holes and electrons are recombined on the emission layer though the hole transport layer (HTL) and the electron transport layer (ETL) to provide light emitting excitons. The provided light emitting excitons emit light by transiting to the ground state.

The light emitting material may be classified as a fluorescent material including singlet excitons and a phosphorescent material including triplet excitons.

The phosphorescent light emitting material may be useful as a light emitting material (D. F. O'Brien et al., Applied Physics Letters, 74 3, 442-444, 1999; M. A. Baldo et al., Applied Physics letters, 75 1, 4-6, 1999). Such phosphorescent emission occurs by transition of electrons from the ground state to the exited state, non-radiative transition of a singlet exciton to a triplet exciton through intersystem crossing, and transition of the triplet exciton to the ground state to emit light.

When the triplet exciton transitions, it cannot directly transition to the ground state. Therefore, the electron spin is flipped, and then it transitions to the ground state. Thus, it provides a characteristic of extended lifetime (emission duration) relative to that of fluorescent emission.

In other words, the duration of fluorescent emission is extremely short (at several nanoseconds), but the duration of phosphorescent emission is relatively long (such as at several microseconds), so that phosphorescent emission provides a characteristic of extending the lifetime (emission duration) to more than that of the fluorescent emission.

Quantum mechanically, when holes injected from the anode are recombined with electrons injected from the cathode to provide light emitting excitons, the singlet and the triplet are produced in a ratio of 1:3, in which the triplet light emitting excitons are produced at three times the amount of the singlet light emitting excitons in the organic light emitting diode.

Accordingly, the percentage of the singlet exited state is 25% (the triplet is 75%) in the case of a fluorescent material, so it has limits in luminous efficiency. On the other hand, in the case of a phosphorescent material, it can utilize 75% of the triplet exited state and 25% of the singlet exited state, so theoretically the internal quantum efficiency can reach up to 100%. When phosphorescent light emitting material is used, it has advantages in an increase in luminous efficiency of around four times that of the fluorescent light emitting material.

In the above-mentioned organic light emitting diode, a light emitting colorant (dopant) may be added in an emission layer (host) in order to increase the efficiency and stability in the emission state. In this structure, the efficiency and properties of the light emission diodes are dependent on the host material in the emission layer.

SUMMARY

Embodiments are directed to a material for an organic photoelectric device, and an organic photoelectric device including the same, which substantially overcome one or more problems due to the limitations and disadvantages of the related art.

It is a feature of an embodiment to provide a material suitable for organic photoelectric device having high luminous efficiency at a low driving voltage.

It is a feature of an embodiment to provide a material for an organic photoelectric device having thermal stability and bipolar characteristics with good hole and electron transporting properties.

At least one of the above and other features and advantages may be realized by providing a material for an organic photoelectric device, the material including a compound represented by the following Formula 1:

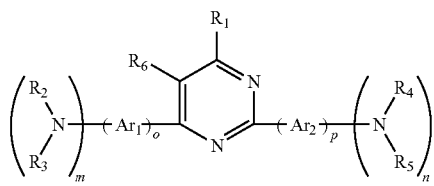

[Formula 1]

wherein, in Formula 1, $Ar_1$ and $Ar_2$ are independently a substituted or unsubstituted C6 to C30 aryl or arylene, a substituted or unsubstituted C1 to C30 alkyl or alkylene, or a substituted or unsubstituted C2 to C30 heteroaryl or heteroarylene, $R_1$ and $R_6$ are independently hydrogen, a substituted or unsubstituted C6 to C30 aryl, a substituted or unsubstituted C2 to C30 heteroaryl, or a substituted or unsubstituted C1 to C30 alkyl, $R_2$ to $R_5$ are independently hydrogen, a substituted or unsubstituted C6 to C30 aryl or arylene, a substituted or unsubstituted C2 to C30 heteroaryl or heteroarylene, or a substituted or unsubstituted C1 to C30 alkyl or alkylene, $R_2$ and $R_3$ are independently separate substituents or are joined together to form a ring, $R_4$ and $R_5$, are independently separate substituents or are joined together to form a ring, m and n are integers ranging from 0 to 3, and m+n is an integer ranging from 1 to 6, and o and p are integers ranging from 0 to 2, and o+p is an integer ranging from 1 to 4.

The compound represented by Formula 1 may be represented by the following Formula 2:

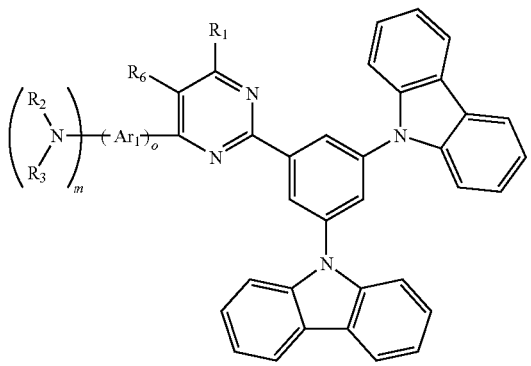

[Formula 2]

wherein, in Formula 2, $Ar_1$ is a substituted or unsubstituted C6 to C30 aryl or arylene, a substituted or unsubstituted C1 to C30 alkyl or alkylene, or a substituted or unsubstituted C2 to C30 heteroaryl or heteroarylene, $R_1$ and $R_6$ are independently hydrogen, a substituted or unsubstituted C6 to C30 aryl, a substituted or unsubstituted C2 to C30 heteroaryl, or a substituted or unsubstituted C1 to C30 alkyl, $R_2$ and $R_3$ are independently hydrogen, a substituted or unsubstituted C6 to C30 aryl or arylene, a substituted or unsubstituted C2 to C30 heteroaryl or heteroarylene, or a substituted or unsubstituted C1 to C30 alkyl or alkylene, and $R_2$ and $R_3$ are independently separate substituents or are joined together to form a ring.

The compound represented by Formula 1 may be represented by the following Formula 3:

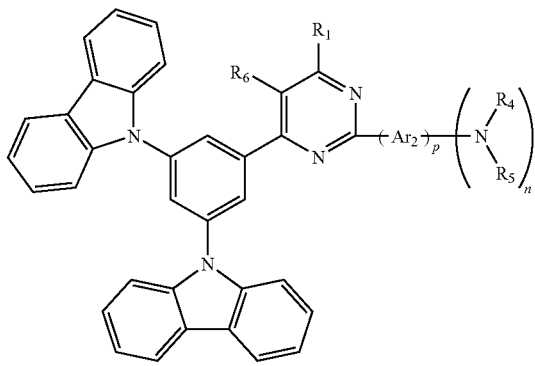

[Formula 3]

wherein, in Formula 3, $Ar_2$ is a substituted or unsubstituted C6 to C30 aryl or arylene, a substituted or unsubstituted C1 to C30 alkyl or alkylene, or a substituted or unsubstituted C2 to C30 heteroaryl or heteroarylene, $R_1$ and $R_6$ are independently hydrogen, a substituted or unsubstituted C6 to C30 aryl, a substituted or unsubstituted C2 to C30 heteroaryl, or a substituted or unsubstituted C1 to C30 alkyl, $R_4$ and $R_5$ are independently hydrogen, a substituted or unsubstituted C6 to C30 aryl or arylene, a substituted or unsubstituted C2 to C30 heteroaryl or heteroarylene, or a substituted or unsubstituted C1 to C30 alkyl or alkylene, and $R_4$ and $R_5$ are independently separate substituents or are joined together to form a ring.

The compound represented by Formula 1 may be a compound represented by any one of the following Formulae 4 to 10:

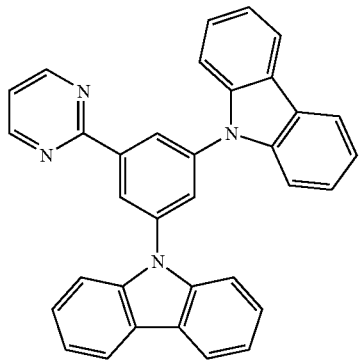

[Formula 4]

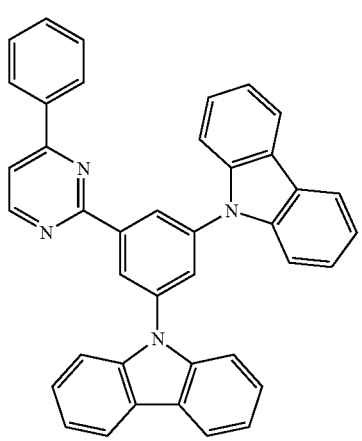

[Formula 5]

[Formula 6]
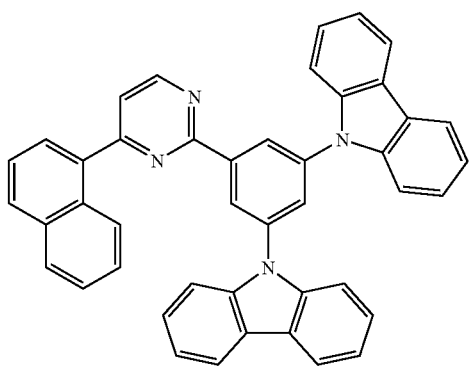
[Formula 7]
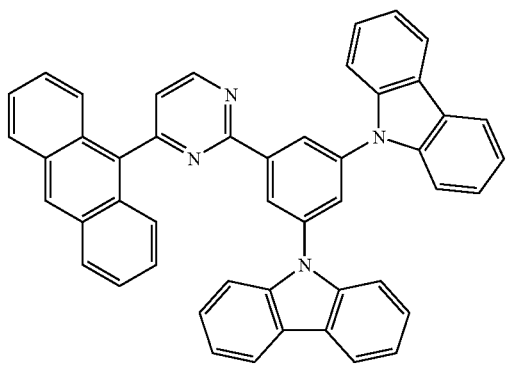
[Formula 8]
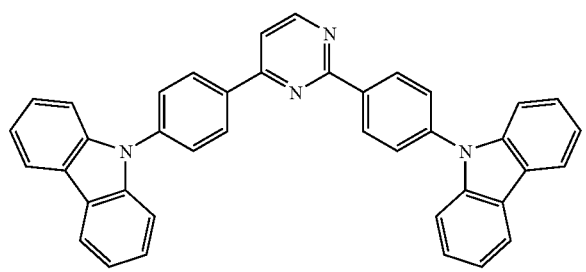
[Formula 9]
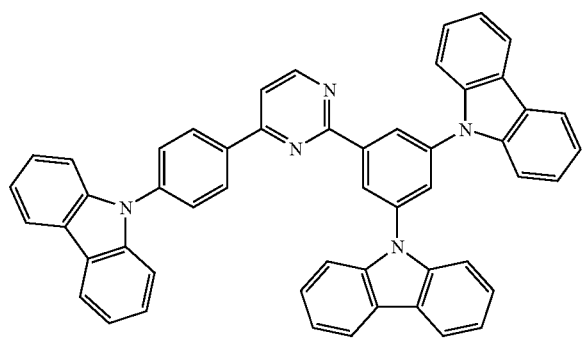
[Formula 10]
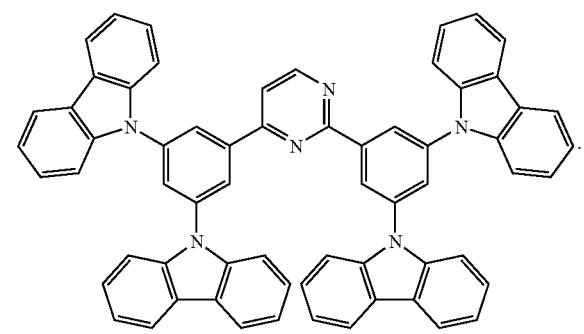
The compound represented by Formula 1 may be a compound represented by any one of the following Formulae 11 to 16:
[Formula 11]
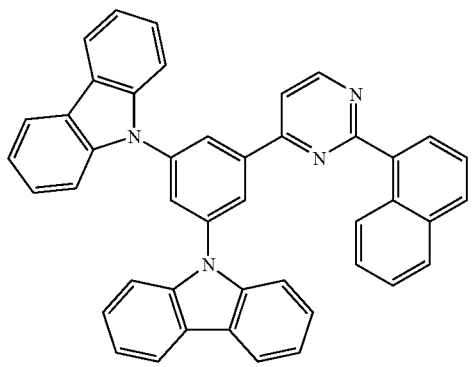
[Formula 12]
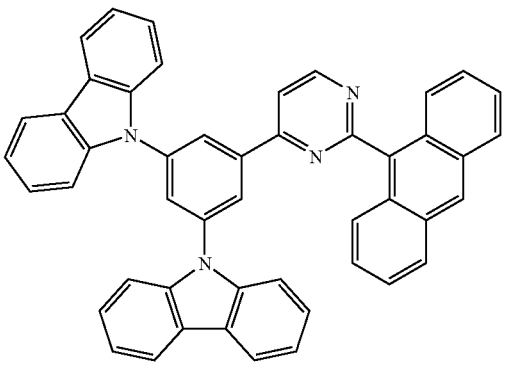
[Formula 13]
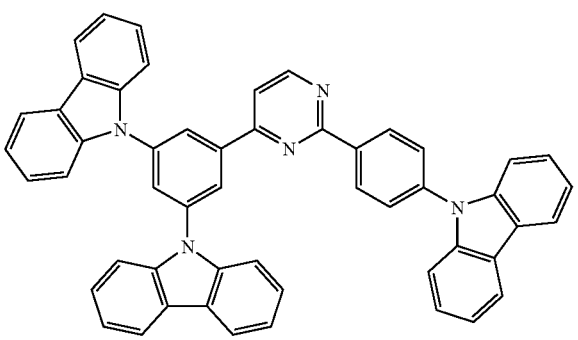

The compound represented by Formula 1 may be a compound represented by any one of the following Formulae 17 to 22:
[Formula 14]
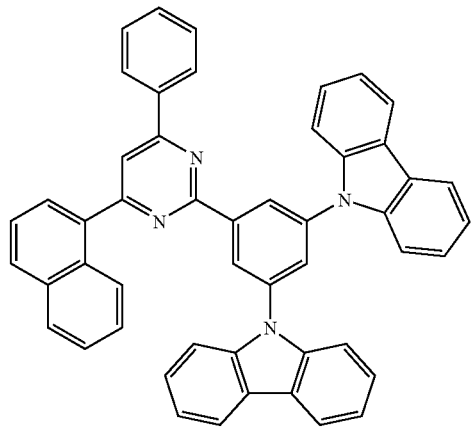
[Formula 15]
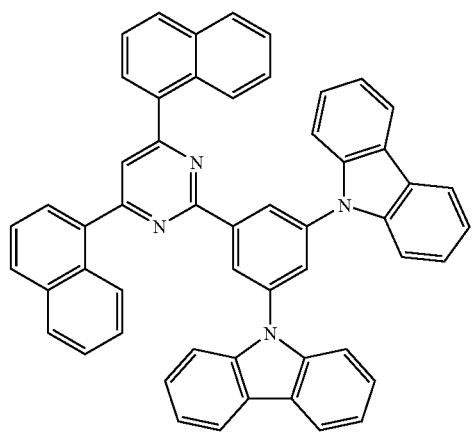
[Formula 16]
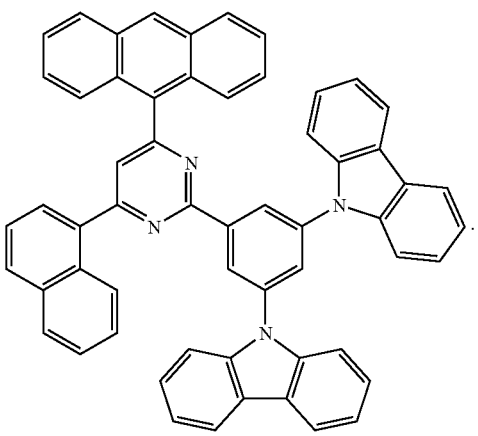
[Formula 17]
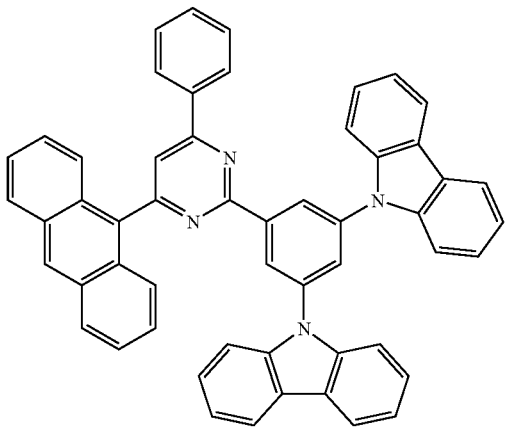
[Formula 18]
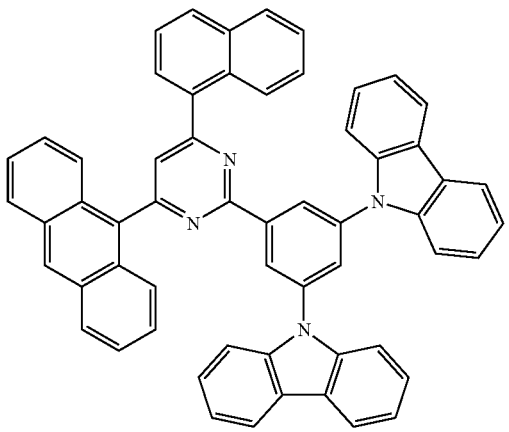
[Formula 19]
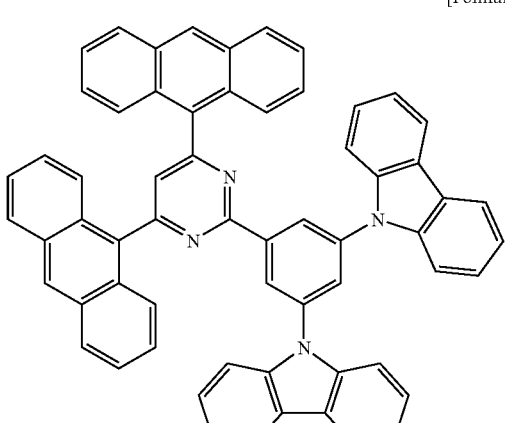

[Formula 20]
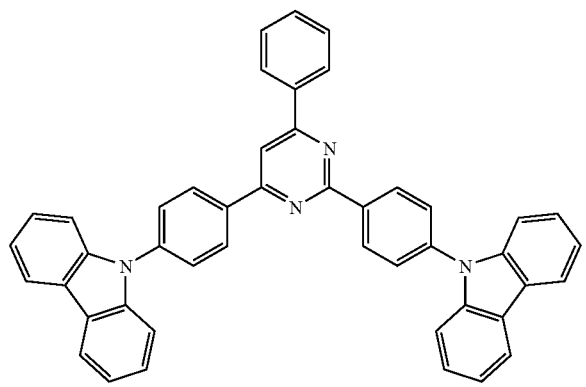
[Formula 21]
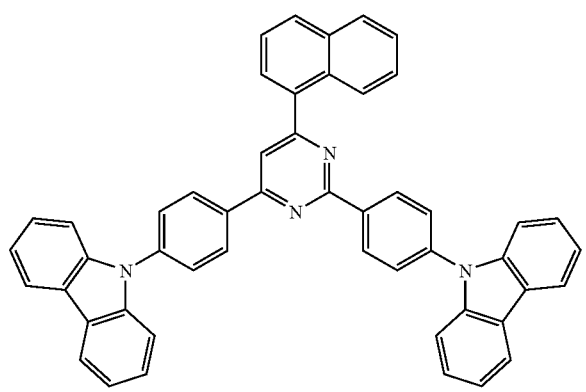
[Formula 22]
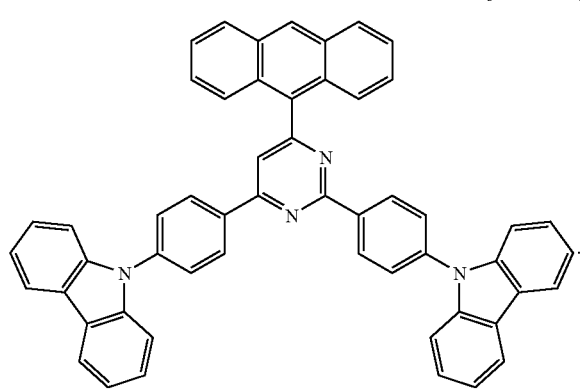
The compound represented by Formula 1 may be a compound represented by any one of the following Formulae 23 to 28:
[Formula 23]
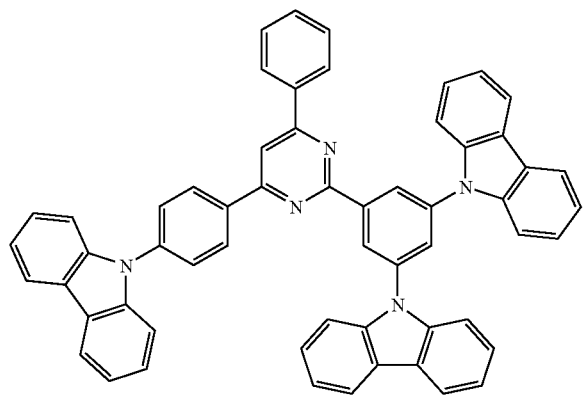
[Formula 24]
[Formula 25]
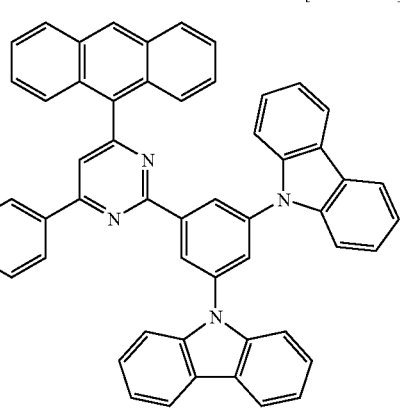

[Formula 26]
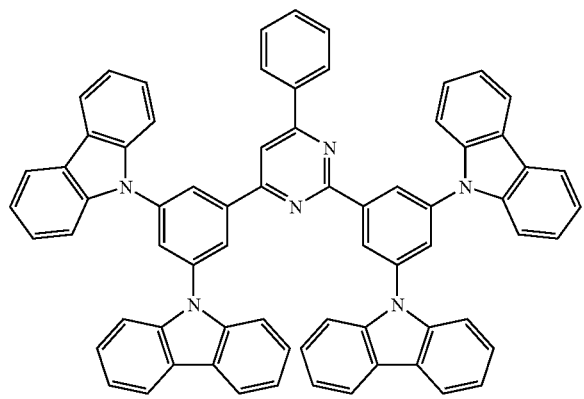
[Formula 27]
[Formula 28]
The compound represented by Formula 1 may be a compound represented by any one of the following Formulae 29 to 34:
[Formula 29]
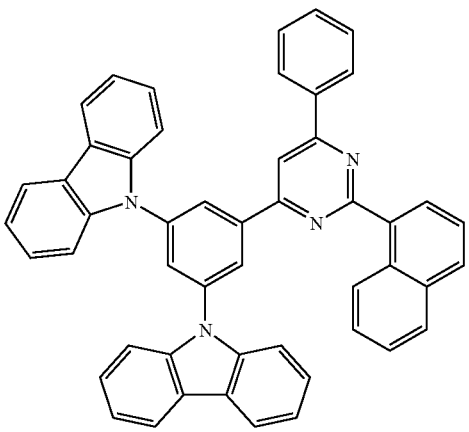
[Formula 30]
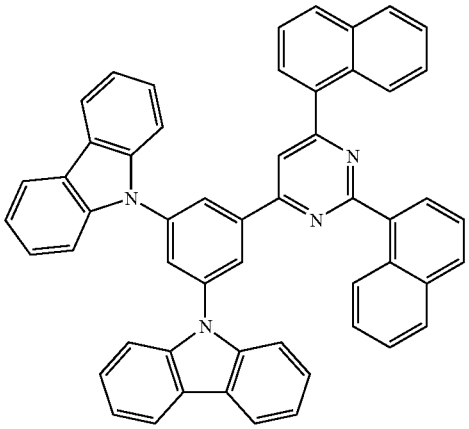
[Formula 31]
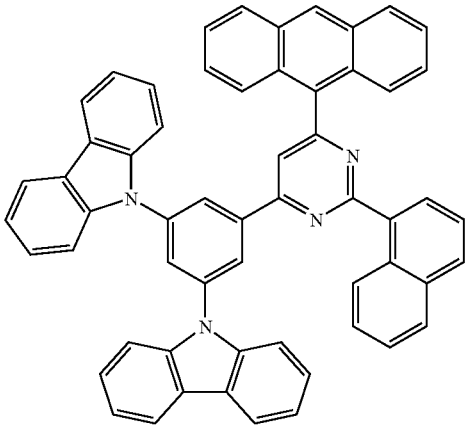

[Formula 32]

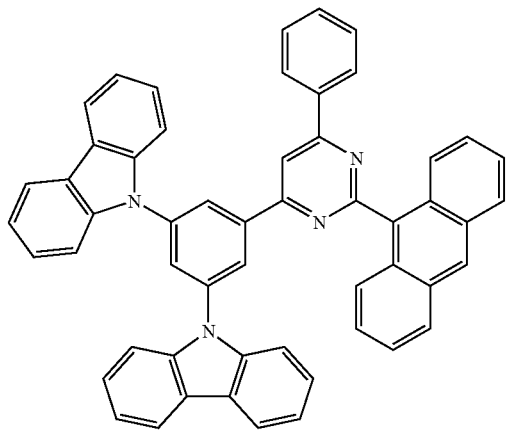

[Formula 33]

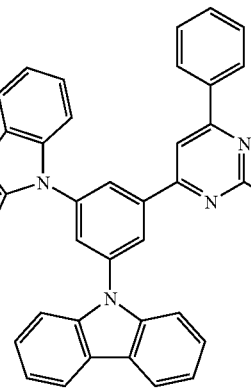

[Formula 34]

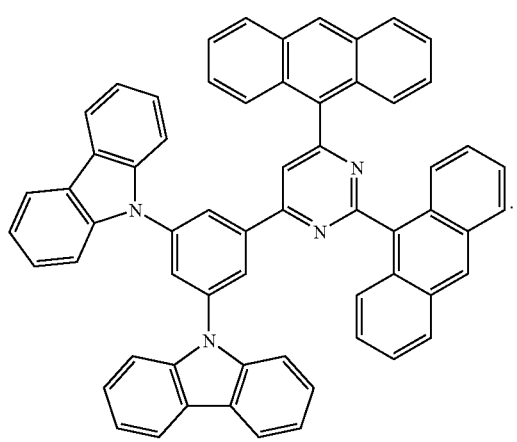

The compound represented by Formula 1 may be a compound represented by any one of the following Formulae 35 to 37:

[Formula 35]

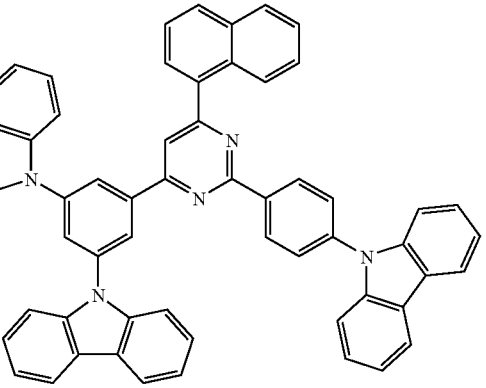

[Formula 36]

[Formula 37]

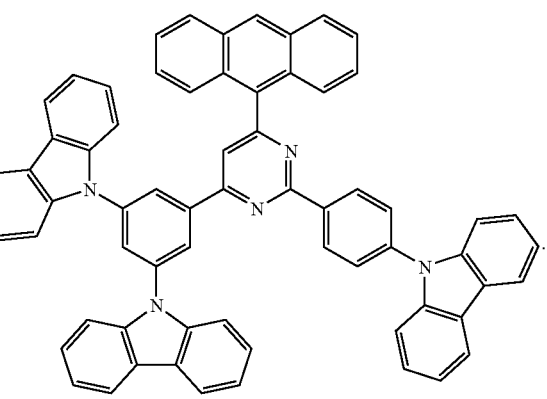

The compound represented by Formula 1 may have a glass transition temperature of about 120° C. or more and has a thermal decomposition temperature of about 400° C. or more.

At least one of the above and other features and advantages may also be realized by providing an organic photoelectric device, including an anode, a cathode, and an organic layer disposed between the anode and cathode, wherein the organic layer includes the material including the compound represented by Formula 1.

The organic layer may be an emission layer.

The compound represented by Formula 1 may be present as a phosphorescent or fluorescent host of the emission layer.

The organic photoelectric device may further include a phosphorescent or fluorescent dopant combined with the host, the dopant being a red, green, blue, or white light emitting dopant.

The compound represented by Formula 1 may be a fluorescent blue dopant in the emission layer.

The organic layer may be an electron transport layer (ETL), an electron injection layer (EIL), or a combination thereof.

The organic layer may be an emission layer, a hole transport layer (HTL), a hole injection layer (HIL), an electron transport layer (ETL), an electron injection layer (EIL), or a combination thereof.

BRIEF DESCRIPTION OF THE DRAWINGS

The above and other features and advantages will become more apparent to those of skill in the art by describing in detail example embodiments with reference to the attached drawings, in which.

Figure 1:
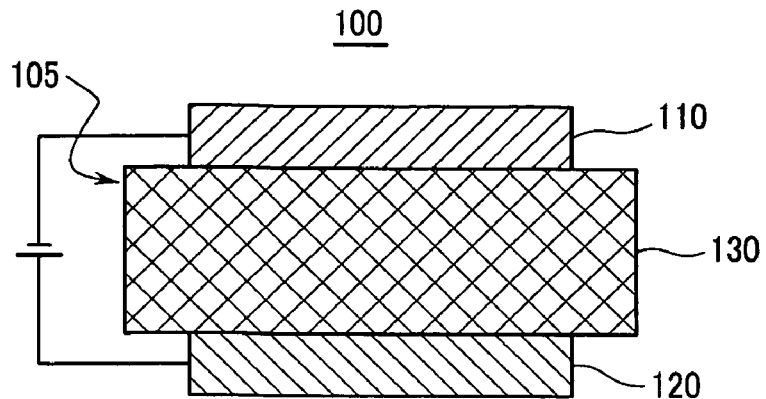
FIGS. 1 to 5 illustrate cross-sectional views of organic photoelectric devices including organic compounds according to various embodiments.

<Description of Reference Numerals in the Drawings>

| | |
|---|---|
| 100: organic photoelectric device | 110: cathode |
| 120: anode | 105: organic thin layer |
| 130: emission layer | 140: hole transport layer |
| 150: electron transport layer (ETL) | 160: electron injection layer (EIL) |
| 170: hole injection layer. | |

DETAILED DESCRIPTION

Korean Patent Application No. 10-2007-0090015, filed on Sep. 5, 2007, in the Korean Intellectual Property Office, and entitled: "Material for Organic Photoelectric Device and Organic Photoelectric Device Including The Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the expressions "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" includes the following meanings: A alone; B alone; C alone; both A and B together; both A and C together; both B and C together; and all three of A, B, and C together. Further, these expressions are open-ended, unless expressly designated to the contrary by their combination with the term "consisting of." For example, the expression "at least one of A, B, and C" may also include an $n^{th}$ member, where n is greater than 3, whereas the expression "at least one selected from the group consisting of A, B, and C" does not.

As used herein, the expression "or" is not an "exclusive or" unless it is used in conjunction with the term "either." For example, the expression "A, B, or C" includes A alone; B alone; C alone; both A and B together; both A and C together; both B and C together; and all three of A, B, and C together, whereas the expression "either A, B, or C" means one of A alone, B alone, and C alone, and does not mean any of both A and B together; both A and C together; both B and C together; and all three of A, B, and C together.

As used herein, the terms "a" and "an" are open terms that may be used in conjunction with singular items or with plural items. For example, the term "a dopant" may represent a single compound, e.g., $Ir(Piq)_2(acac)$, or multiple compounds in combination, e.g., $Ir(Piq)_2(acac)$ mixed with PtOEP.

Embodiments relate to a material for an organic photoelectric device and an organic photoelectric device including the same. The material may provide thermal stability, have good hole and electron transporting properties, and be suitable for a high efficiency organic photoelectric device.

The material may be used alone, may be used as a host material in combination with a dopant, etc. The material may include a symmetric or asymmetric compound represented by the following Formula 1. The compound represented by Formula 1 may be used with other compounds represented by Formula 1 in a mixture of respective compounds of Formula 1, each of which is different from the others. The compound represented by Formula 1 may be a bipolar organic compound including both a hole transporting unit and an electron transporting unit.

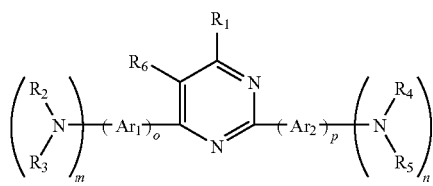

[Formula 1]

In Formula 1, $Ar_1$ and $Ar_2$ may be independently a substituted or unsubstituted C6 to C30 aryl or arylene, a substituted or unsubstituted C1 to C30 alkyl or alkylene, or a substituted or unsubstituted C2 to C30 heteroaryl or heteroarylene.

In Formula 1, $R_1$ and $R_6$ may be independently a substituted or unsubstituted C6 to C30 aryl, a substituted or unsubstituted C2 to C30 heteroaryl, or a substituted or unsubstituted C1 to C30 alkyl.

In Formula 1, $R_2$ to $R_5$ may be independently a substituted or unsubstituted C6 to C30 aryl or arylene, a substituted or unsubstituted C2 to C30 heteroaryl or heteroarylene, or a substituted or unsubstituted C1 to C30 alkyl or alkylene, In Formula 1, $R_2$ and $R_3$, and $R_4$ and $R_5$, may be independently separate substituents or may be joined together, e.g., fused together, to form a ring or cyclic structure.

In Formula 1, m and n may be integers ranging from 0 to 3, and m+n may be an integer ranging from 1 to 6.

In Formula 1, o and p may be integers ranging from 0 to 2, and o+p may be an integer ranging from 1 to 4.

In the present specification, when specific definition is not provided, the substituted aryl, substituted arylene, substituted alkyl, substituted alkylene, substituted heteroaryl, or substituted heteroarylene respectively refers to an aryl, an arylene, an alkyl, an alkylene, a heteroaryl, or a heteroarylene substituted with a C1 to C30 alkyl, a halogen, a C1 to C30 haloalkyl, a C6 to C30 aryl, or a C2 to C30 heteroaryl.

In the present specification, the heteroaryl or heteroarylene respectively refers to an aryl, and an arylene including 1 to 3 heteroatoms selected from the group consisting of nitrogen (N), oxygen (O), sulfur (S), and phosphorus (P), and the remainder being carbon.

In Formula 1, the pyrimidine ($C_6H_4N_2$) functions as an electron transporting unit, and side chains linked to $Ar_1$ and $Ar_2$ function as an electron transporting unit.

The bipolar organic compound of the above Formula 1 may be represented by asymmetric organic compounds of the following Formula 2 or Formula 3, which may be used alone or in mixtures thereof in a material for an organic photoelectric device.

In Formulae 2 and 3, $Ar_1$ and $Ar_2$ may be independently a substituted or unsubstituted C6 to C30 aryl or arylene, a substituted or unsubstituted C1 to C30 alkyl or alkylene, or a substituted or unsubstituted C2 to C30 heteroaryl or heteroarylene.

In Formulae 2 and 3, $R_1$ and $R_6$ may be independently hydrogen, a substituted or unsubstituted C6 to C30 aryl, a substituted or unsubstituted C2 to C30 heteroaryl, or a substituted or unsubstituted C1 to C30 alkyl.

In Formulae 2 and 3, $R_2$ to $R_5$ may be independently hydrogen, a substituted or unsubstituted C6 to C30 aryl or arylene, a substituted or unsubstituted C2 to C30 heteroaryl or heteroarylene, or a substituted or unsubstituted C1 to C30 alkyl or alkylene.

In Formulae 2 and 3, $R_2$ and $R_3$, and $R_4$ and $R_5$, may be independently separate substituents or may be fused together to form a ring.

According to various embodiments, compounds represented by Formula 1 may be bipolar organic compounds represented by the following Formulae 4 to 37, which may be used alone or in mixtures thereof in a material for an organic photoelectric device.

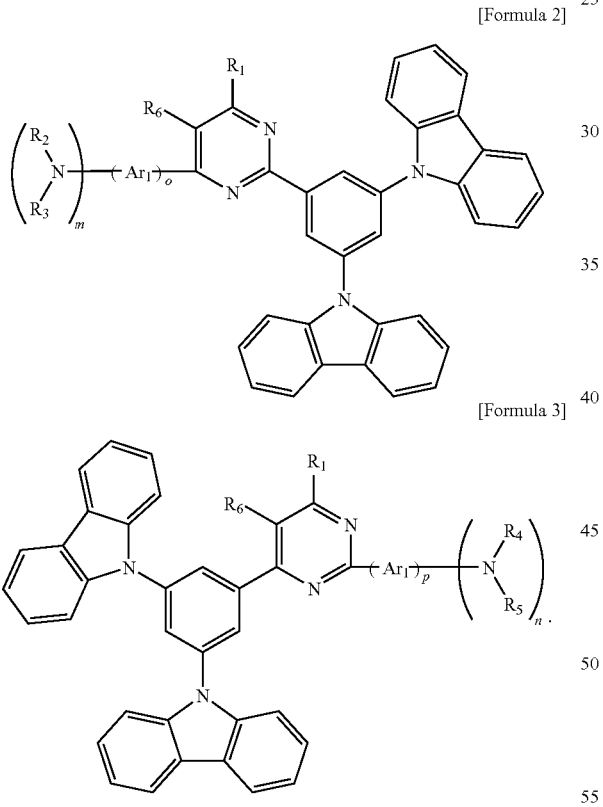

[Formula 7]
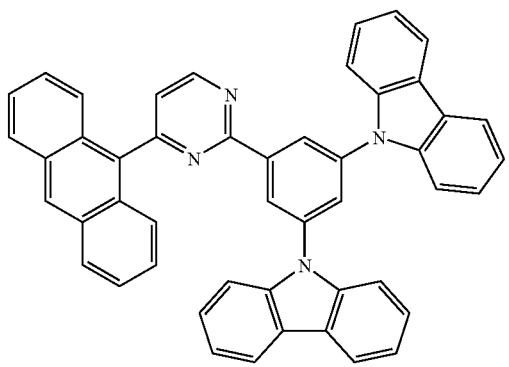
[Formula 8]
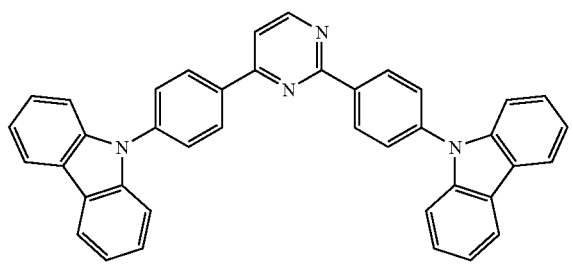
[Formula 9]
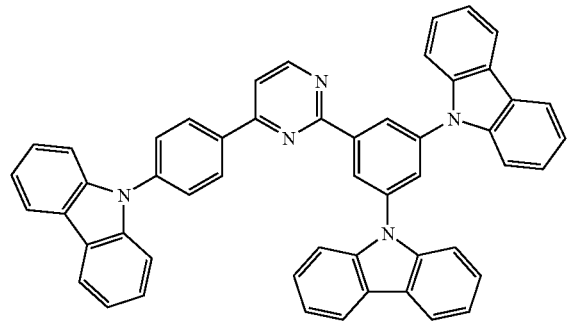
[Formula 10]
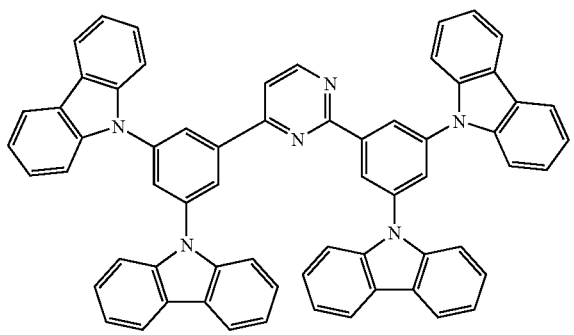
[Formula 11]
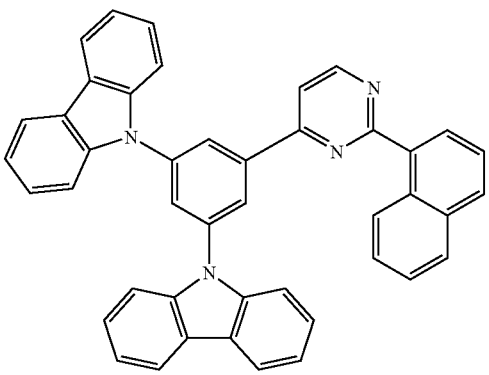
[Formula 12]
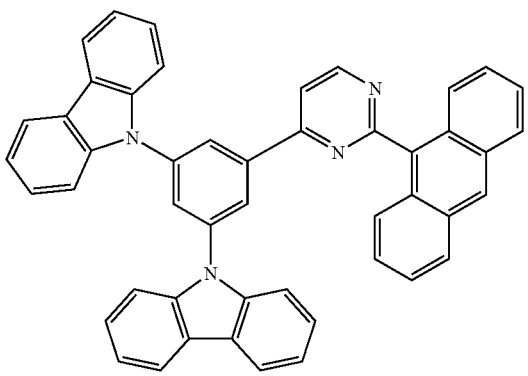
[Formula 13]
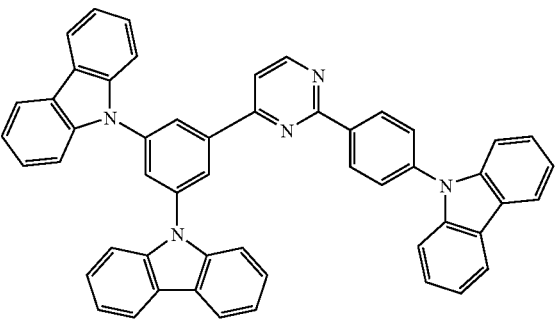
[Formula 14]
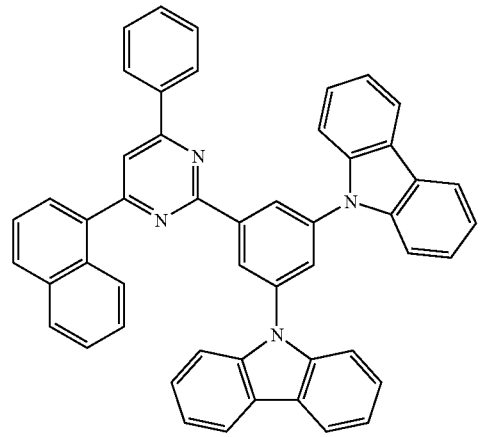

[Formula 15]
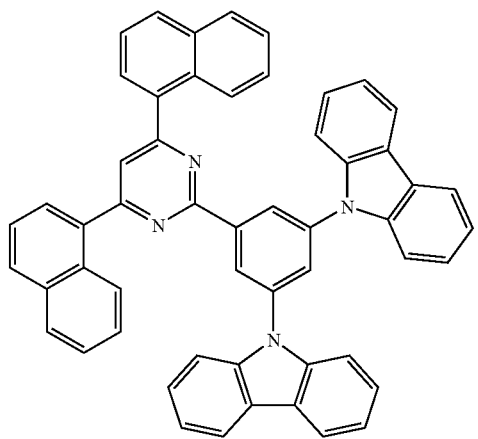
[Formula 16]
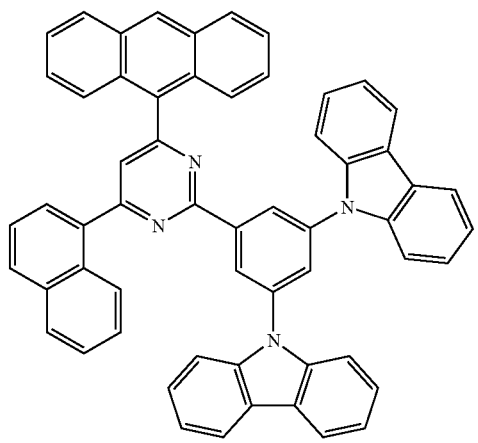
[Formula 17]
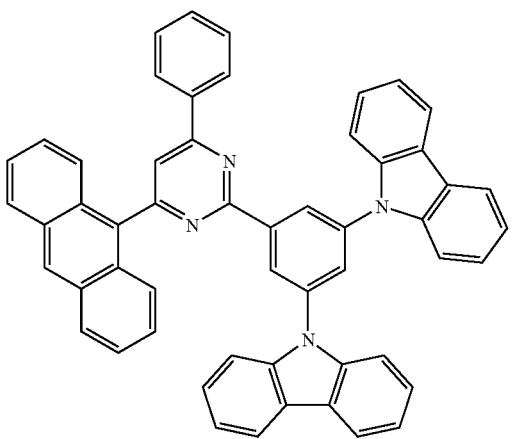
[Formula 18]
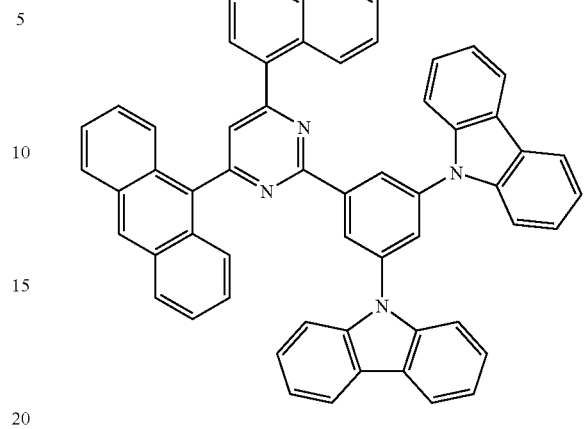
[Formula 19]
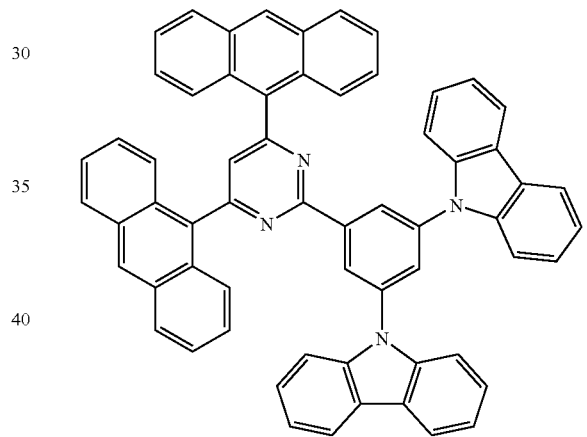
[Formula 20]
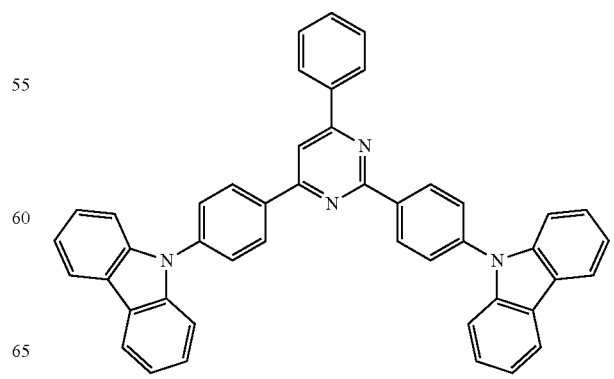

[Formula 21]
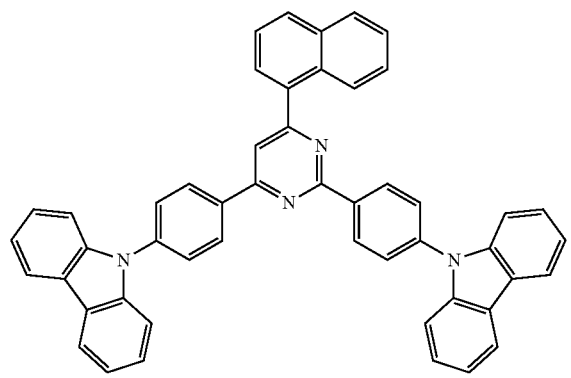
[Formula 22]
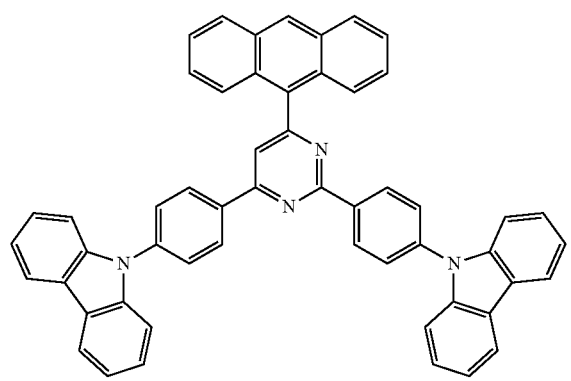
[Formula 23]
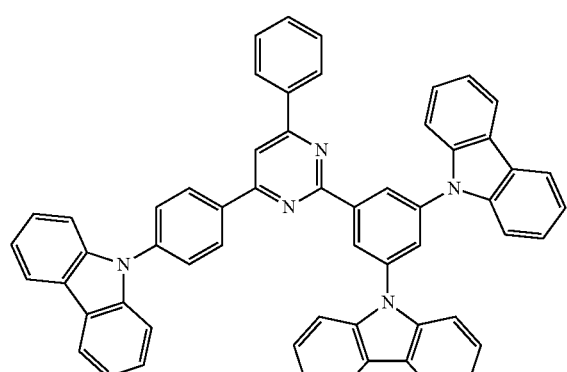
[Formula 24]
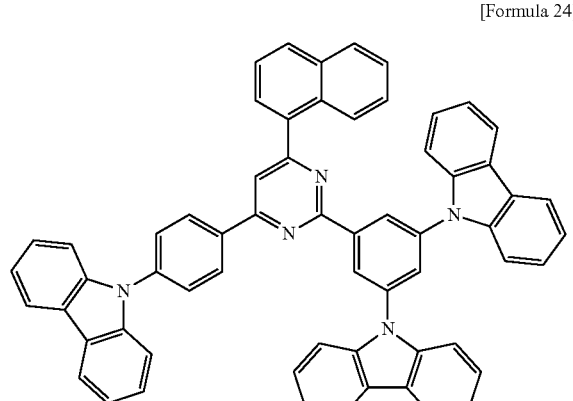
[Formula 25]
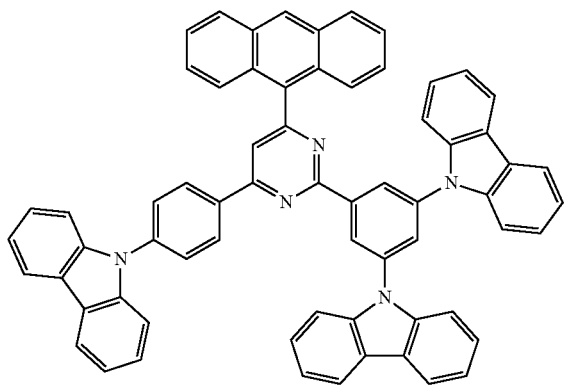
[Formula 26]
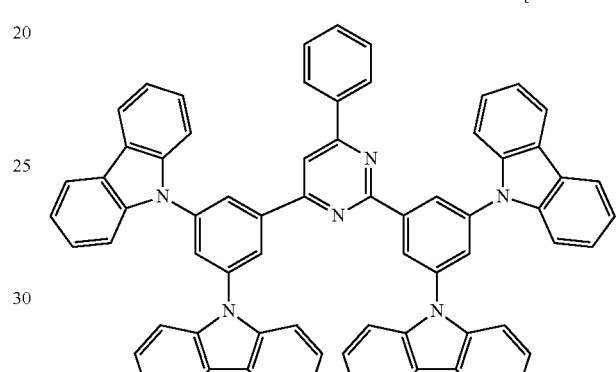
[Formula 27]
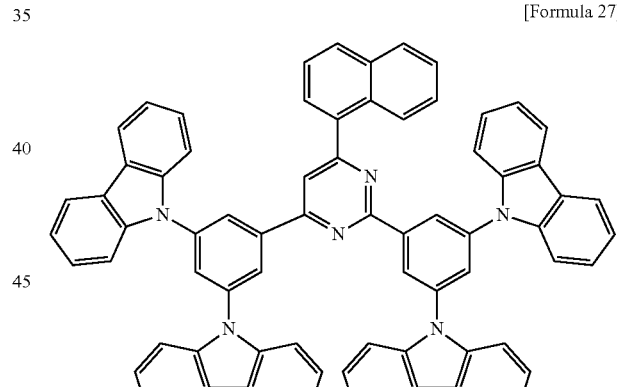
[Formula 28]
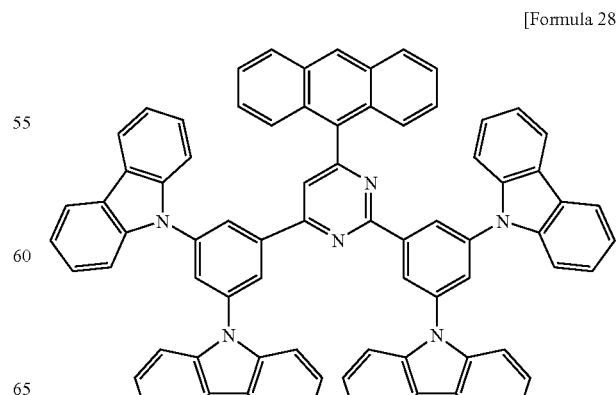

[Formula 29]
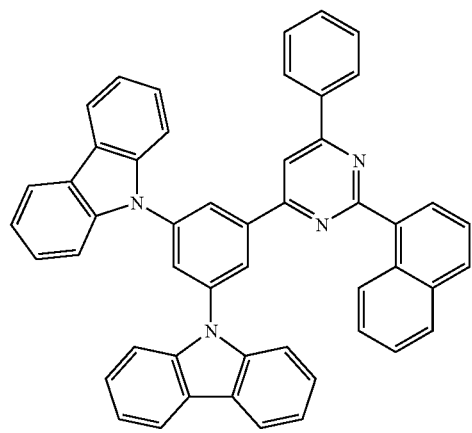
[Formula 30]
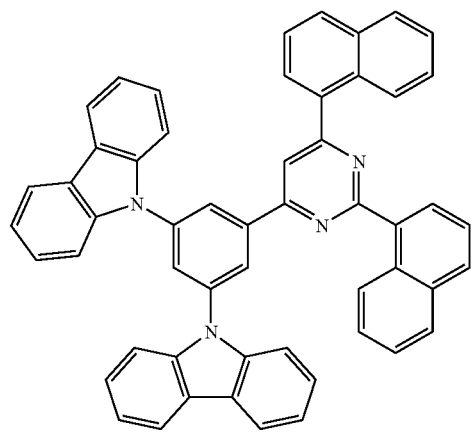
[Formula 31]
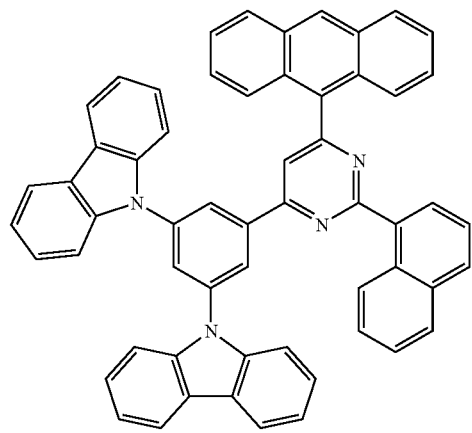
[Formula 32]
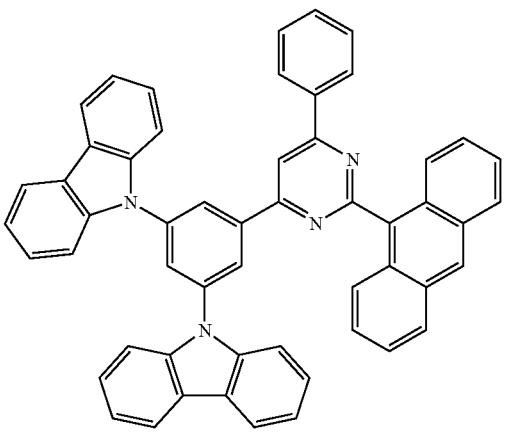
[Formula 33]
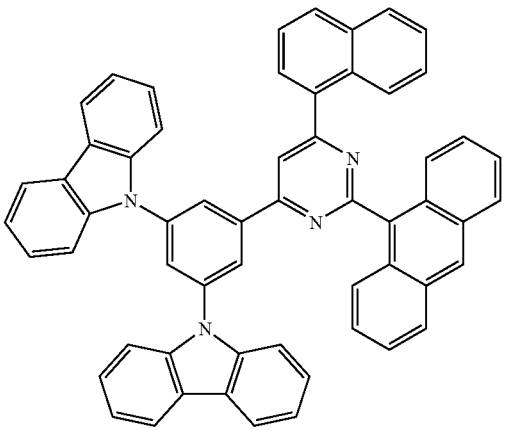
[Formula 34]
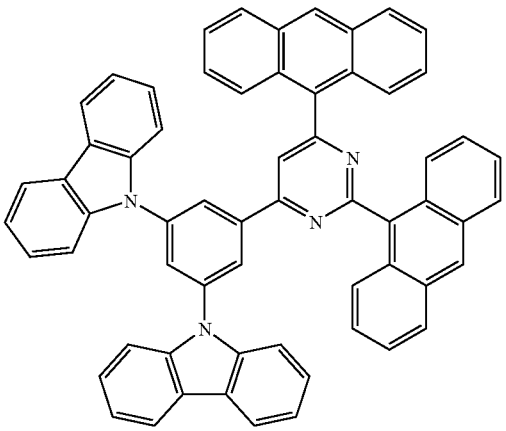

-continued

[Formula 35]

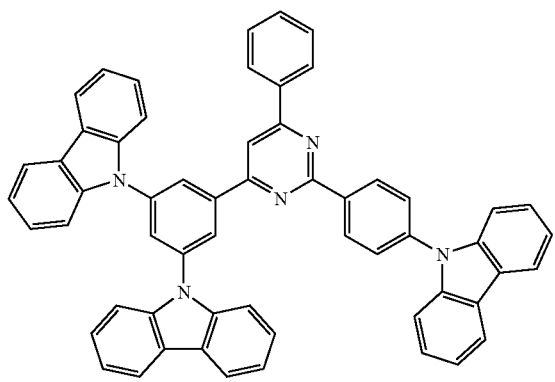

[Formula 36]

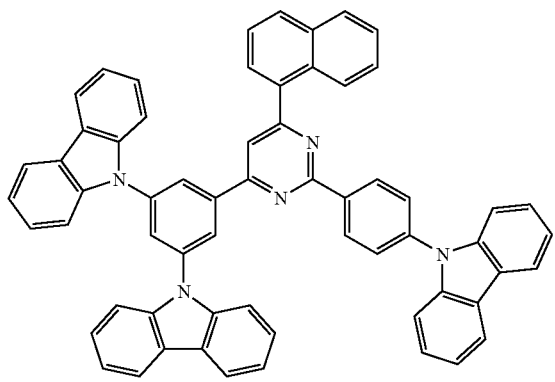

[Formula 37]

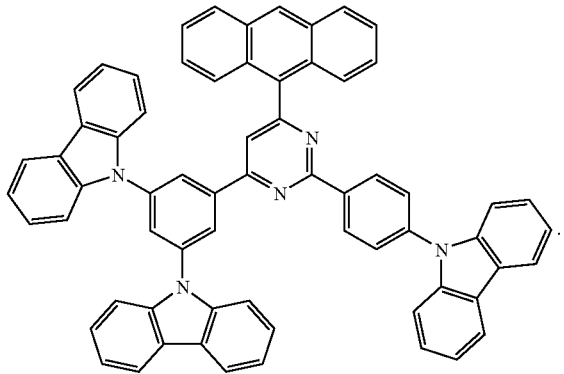

The compound represented by Formula 1 may have a glass transition temperature ($T_g$) of about 120° C. or more. The compound represented by Formula 1 may have a thermal decomposition temperature ($T_d$) of about 400° C. or more. Thus, the compound represented by Formula 1 may have a high thermal stability.

The compound represented by Formula 1 may be included in one or more of the following layers: an emission layer, an electron transport layer (ETL), an electron injection layer (EIL), a hole transport layer (HTL), a hole injection layer (HIL), and a hole blocking layer.

In an implementation, the compound represented by Formula 1 may be used, e.g., by itself, in an electron transport layer (ETL), an electron injection layer (EIL), a hole transport layer (HTL), a hole injection layer (HIL), or a hole blocking layer. In an implementation, the compound represented by Formula 1 may be used in combination with a dopant in an emission layer.

The dopant may be a compound having a high emission property by itself. The dopant may be added to a host in a minor amount. The dopant may also be called a guest. Thus, the dopant may be a material that is doped to the host material to emit light. The dopant may include a metal complex that emits light due to multiplet excitation into a triplet or higher state.

When the organic compounds represented by Formulae 1 to 5 are used for a light emitting host material, all red (R), green (G), and blue (B) colors and white (W) fluorescent or phosphorescent dopant materials may be suitable for a dopant. According to one embodiment, the dopant includes a phosphorescent dopant material. The material may have high light emitting quantum efficiency, may be rarely agglomerated, and may be distributed uniformly in the host material.

The phosphorescent dopant may be an organic metal compound including one or more of the following elements: Ir, Pt, Os, Ti, Zr, Hf, Eu, Tb, and Tm.

The red phosphorescent dopant may include PtOEP (platinum octaethylporphine), Ir(Piq)$_2$(acac) (Piq=1-phenylisoquinoline, acac=pentane-2,4-dione), Ir(Piq)$_3$, and RD 61 from UDC; the green phosphorescent dopant may include Ir(PPy)$_3$ (PPy=2-phenylpyridine), Ir(PPy)$_2$(acac), and GD48 from UDC; and the blue phosphorescent dopant may include (4,6-F$_2$PPy)$_2$Irpic (reference: Appl. Phys. Lett., 79, 2082-2084, 2001).

Another embodiment provides an organic photoelectric device that includes an organic thin layer including the above-described material between an anode and a cathode. In an embodiment, the organic photoelectric device may be an organic light emitting diode.

FIGS. 1 to 5 illustrate cross-sectional views of organic photoelectric devices including organic compounds according to various embodiments.

Referring to FIGS. 1 to 5, the respective organic photoelectric devices 100, 200, 300, 400, and 500 illustrated therein may include at least one organic thin layer 105 interposed between the anode 120 and cathode 110. The anode 120 may include an ITO (indium tin oxide) transparent electrode. The cathode 110 may include a metal electrode such as aluminum.

Referring to FIG. 1, the organic photoelectric device 100 may include an organic thin layer 105 including only an emission layer 130.

Figure 2:
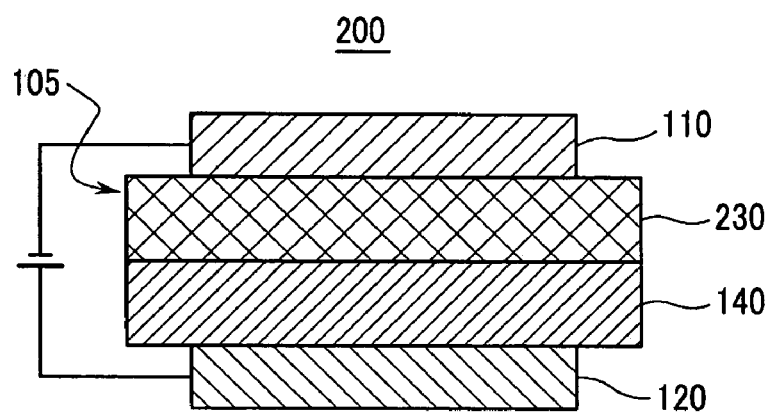

Referring to FIG. 2, a double-layered organic photoelectric device 200 may include an organic thin layer 105 including an emission layer 230 including an electron transport layer (ETL) (not shown), and a hole transport layer (HTL) 140. The hole transport layer (HTL) 140 may be a separate layer having an excellent binding property with a transparent electrode such as ITO, or an excellent hole transporting property.

Figure 3:
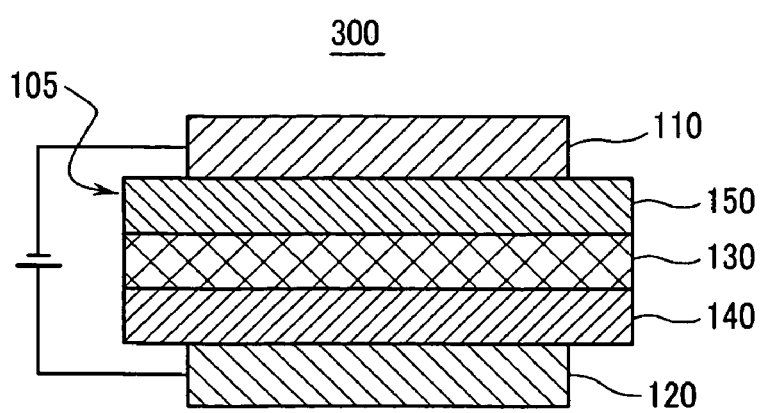

Referring to FIG. 3, a three-layered organic photoelectric device 300 may include the organic thin layer 105 including an electron transport layer (ETL) 150, an emission layer 130, and a hole transport layer (HTL) 140. The emission layer 130 may be independently provided, and layers having an excellent electron transporting property or an excellent hole transporting property may be separately stacked.

Figure 4:
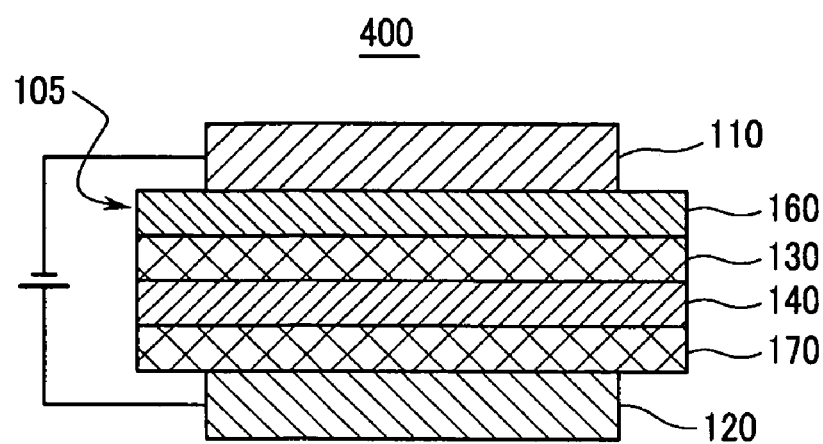

As shown in FIG. 4, a four-layered organic photoelectric device 400 may include the organic thin layer 105 including an electron injection layer (EIL) 160, an emission layer 130, a hole transport layer (HTL) 140, and a hole injection layer (HIL) 170 for binding with the cathode of ITO.

Figure 5:
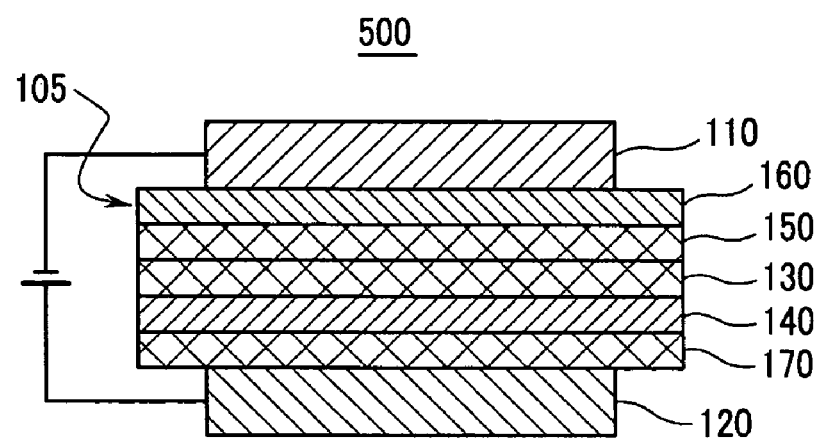

As shown in FIG. 5, a five layered organic photoelectric device 500 may include the organic thin layer 105 including an electron transport layer (ETL) 150, an emission layer 130, a hole transport layer (HTL) 140, and a hole injection layer (HIL) 170, and may further include an electron injection layer (EIL) 160 to achieve low voltage.

In order to form the organic thin layer 105 having one to five layers, the method may follow a dry coating method such as evaporation, sputtering, plasma plating, and ion plating, or a wet coating method such as spin coating, dipping, and flow coating.

In an embodiment, at least one layer of the emission layer, electron transport layer (ETL), electron injection layer (EIL), hole transport layer (HTL), hole injection layer (HIL), hole blocking layer includes the above-described material including the compound represented by Formula 1 for the organic photoelectric device.

The organic thin layer may include a phosphorescent light emitting compound such as a metal complex that emits light due to the multiple excitation into a triplet or higher state.

The following Examples and Comparative Examples are provided in order to set forth particular details of one or more embodiments. However, it will be understood that the embodiments are not limited to the particular details described.

(Synthesis of Material for an Organic Photoelectric Device)

EXAMPLE 1-1

Synthesis of Organic Compound (5)

A bipolar organic compound (5) as a material for an organic photoelectric device was synthesized as shown in the following Reaction Scheme 1.

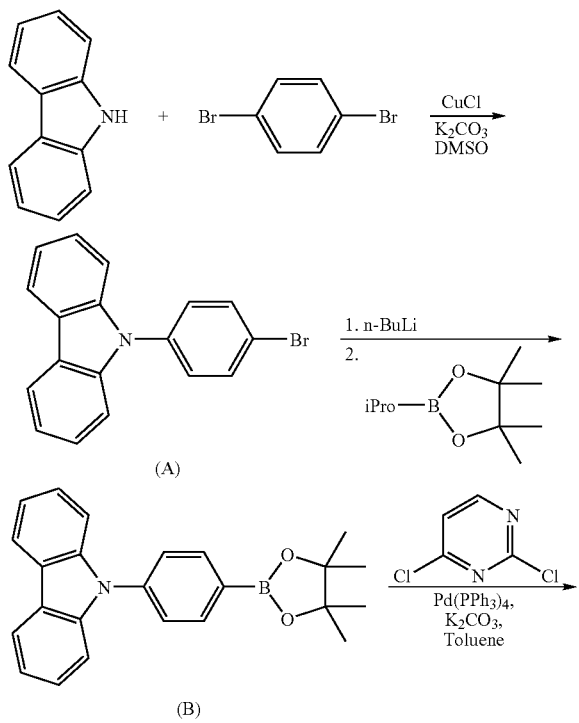

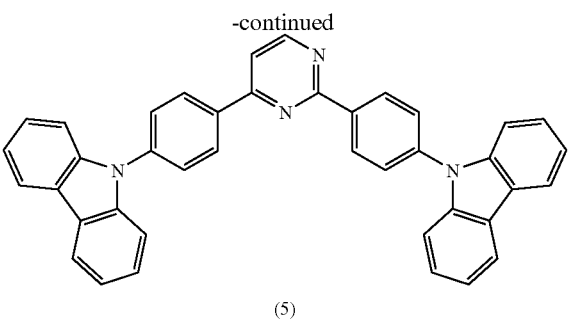

(5)

Step 1: Synthesis of First Intermediate (A)

50.8 g (304 mmol) of carbazole, 71.6 g (304 mmol) of 1,4-dibromobenzene, 3.76 g (38 mmol) of cuprous chloride, and 83.9 g (607 mmol) of potassium carbonate were suspended in 322 ml of dimethylsulfoxide, and refluxed under a nitrogen atmosphere for 8 hours while heating. The refluxed reaction fluid was cooled to room temperature and recrystallized with methanol.

The precipitated crystals were separated by filtration and the obtained residue was purified by silica gel column chromatography, providing 59.9 g of the first crystalline intermediate (A) (yield 61.3%).

Step 2: Synthesis of Second Intermediate (B)

37.8 g (117 mmol) of the first intermediate product (A) was dissolved in 378 ml of tetrahydrofuran, then 100.5 ml (161 mmol) of n-butyl lithium hexane solution (1.6 M) was added thereto under an argon atmosphere at −70° C. The obtained solution was agitated at −70° C. to 40° C. for 1 hour. The agitated reaction fluid was frozen to −70° C., and 47.9 ml (235 mmol) of isopropyltetramethyl dioxaborolane was slowly added thereto in a dropwise fashion. The obtained solution was agitated at −70° C. for 1 hour and heated to room temperature, and then agitated for 6 hours. To the obtained reaction solution, 200 ml of water was added and agitated for 20 minutes.

The agitated reaction solution was separated into two liquid layers, and an organic layer thereof was dried with anhydrous sodium sulfate. After the organic solvent was removed under a reduced pressure, the obtained residue was purified with silica gel column chromatography to provide 28.9 g of the second crystalline intermediate (B) (yield 66.7%).

Step 3: Synthesis of Compound (5)

11.5 g (31 mmol) of the second intermediate (B), 2.1 g (14 mmol) of 2,4-dichloropyrimidine, and 0.81 g (0.7 mmol) of tetrakis-(triphenylphosphine)palladium were suspended in 63 ml of tetrahydrofuran and 42 ml of toluene, then added with a solution of 7.8 g (56 mmol) of sodium carbonate dissolved in 42 ml of water. The obtained mixture was heated and refluxed for 12 hours.

The refluxed reaction fluid was separated into two layers, and an organic layer thereof was cleaned with a sodium chloride saturated aqueous solution and dried with anhydrous sodium sulfate. Subsequently, the organic solvent was removed by distillation under reduced pressure, and the residue was recrystallized with toluene. The precipitated crystals were separated by filtration and cleaned with toluene to provide 5.5 g (69.3%) of the crystalline organic compound (5).

EXAMPLE 1-2

Synthesis of Organic Compound (10)

A bipolar organic compound (10) having the above Formula 13 as a material for an organic photoelectric device was synthesized as shown in the following Reaction Scheme 2.

[Reaction Scheme 2]
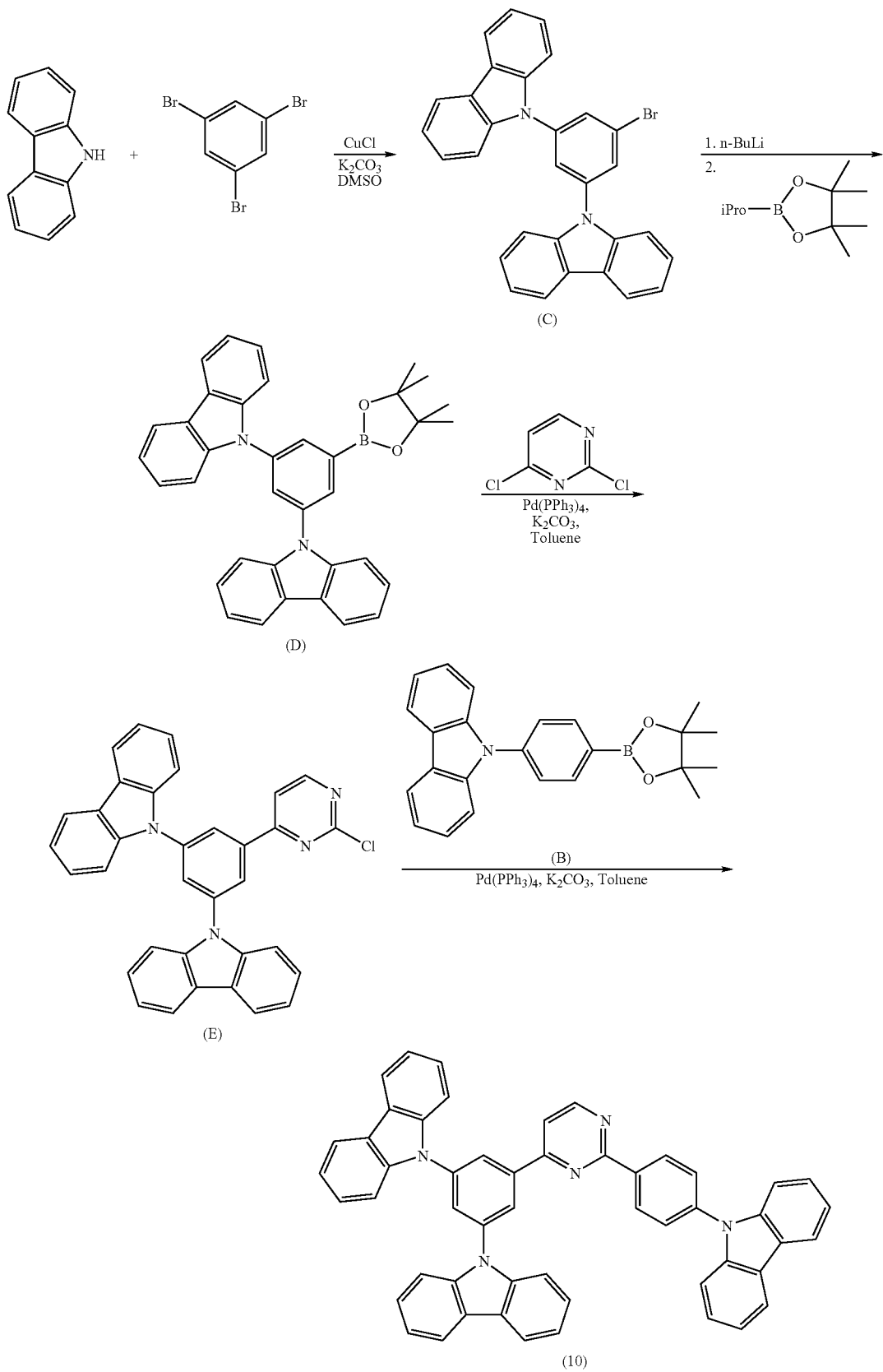

Step 1; Synthesis of First Intermediate (C)

40.4 g (241 mmol) of carbazole, 38.0 g (121 mmol) of 1,3,5-tribromobenzene, 2.99 g (30 mmol) of cuprous chloride, and 66.7 g (483 mmol) of potassium carbonate were suspended in 171 ml of dimethyl sulfoxide, and heated and refluxed under a nitrogen atmosphere for 8 hours.

The refluxed reaction fluid was cooled to room temperature and recrystallized with methanol. The precipitated crystals were separated by filtration and the obtained residue was purified by silica gel column chromatography, providing 59.9 g of the first crystalline intermediate (C) (yield 62.4%).

Step 2: Synthesis of Second Intermediate (D)

35.0 g (72 mmol) of the first intermediate (C) was dissolved in 350 ml of tetrahydrofuran, then 61.5 ml (98 mmol) of n-butyl lithium hexane solution (1.6 M) was added thereto under an argon atmosphere at −70° C. The obtained solution was agitated at −70° C. to 40° C. for 1 hour. The reaction fluid was frozen to −70° C., and 29.3 ml (144 mmol) of isopropyltetramethyl dioxaborolane was slowly added thereto in a dropwise fashion. The obtained solution was agitated at −70° C. for 1 hour and heated to room temperature, and then agitated for 6 hours. To the obtained reaction solution, 200 ml of water was added and agitated for 20 minutes.

The reaction solution was separated into two liquid layers, and an organic layer thereof was dried with anhydrous sodium sulfate. After the organic solvent was removed under a reduced pressure, the obtained residue was purified with silica gel column chromatography to provide 28.9 g of the second crystalline intermediate (D) (yield 65.4%).

Step 3; Synthesis of Third Intermediate (E)

71.7 g (134 mmol) of the second intermediate (D), 20.0 g (134 mmol) of 2,4-dichloropyrimidine, and 3.88 g (25 mmol) of tetrakis-(triphenylphosphine)palladium were suspended in 600 ml of tetrahydrofuran and 400 ml of toluene, then added with a solution of 37.1 g (268 mmol) of potassium carbonate dissolved in 400 ml of water. The obtained mixture was heated and refluxed for 9 hours. The refluxed reaction fluid was separated into two layers, and an organic layer thereof was cleaned with a sodium chloride saturated aqueous solution and dried with anhydrous sodium sulfate.

Subsequently, the organic solvent was removed by distillation under reduced pressure, and the residue was recrystallized with toluene. The precipitated crystals were separated by filtration and cleaned with toluene to provide 42.5 g (60.8%) of the crystalline third intermediate (E).

Step 4; Synthesis of Organic Compound (10)

7.84 g (21 mmol) of the second intermediate (B) in Example 1-1, 10.06 g (19 mmol) of the third intermediate (E), and 0.67 g (0.3 mmol) of tetrakis-(triphenylphosphine)palladium were suspended in 300 ml of tetrahydrofuran and 200 ml of toluene, then added with a solution of 5.34 g (39 mmol) of potassium carbonate dissolved in 200 ml of water. The obtained mixture was heated and refluxed for 9 hours.

The refluxed reaction fluid was separated into two layers, and an organic layer thereof was cleaned with a sodium chloride saturated aqueous solution and dried with anhydrous sodium sulfate. Subsequently, the organic solvent was removed by distillation under reduced pressure, and the residue was recrystallized with toluene. The precipitated crystals were separated by filtration and cleaned with toluene to provide 11.3 g (80.4%) of the crystalline organic compound (10).

(Fabrication of Organic Photoelectric Device)

EXAMPLE 2-1

The organic compound (5) prepared from Example 1-1 was used as a host, and $Ir(piq)_2(acac)$ was used as a dopant to provide an organic photoelectric device.

ITO was provided in a thickness of 1000 Å for an anode, and aluminum (Al) was provided in a thickness of 1000 Å for a cathode.

The method of manufacturing an organic photoelectric device may be described in detail as follows: cutting an ITO glass substrate having a sheet resistance value of 15 Ψ/cm² into a size of 50 mm×50 mm×0.7 mm for a cathode; ultrasonic wave cleaning the same in acetone, isopropyl alcohol, and pure water for 15 minutes, respectively; and UV ozone cleaning for 30 minutes.

N,N'-di(1-naphthyl)-N,N'-diphenylbenzidine (NPD) was deposited on the upper surface of the substrate under the conditions of a vacuum degree of $650 \times 10^{-7}$ Pa and a deposition speed of 0.1 to 0.3 nm/s to provide a 300 Å-thick hole transport layer (HTL).

Subsequently, under the same vacuum deposition conditions, the organic compound (5) and the phosphorescent dopant $Ir(piq)_2(acac)$ were simultaneously deposited to provide an emission layer having a thickness of 300 Å.

During this process, a phosphorescent dopant was deposited at the same time, and the adding amount of the phosphorescent dopant was adjusted to 5 wt % based on the total weight of the emission layer.

Bis(2-methyl-8-quinolinolate)-4-(phenylphenolate)aluminum (BAlq) was deposited on the upper surface of the emission layer under the same vacuum deposition conditions to provide a hole blocking layer having a thickness of 50 Å. Subsequently, $Alq_3$ was deposited under the same vacuum deposition conditions to provide an electron transport layer having a thickness of 200 Å. On the upper surface of the electron transport layer, LiF and Al were sequentially deposited to provide an organic photoelectric device.

The organic photoelectric device has the following five-layered structure: ITO/NPD 300 Å/organic compound 5+Ir(piq)$_2$(acac) (5 wt %, 300 Å)/BAlq 50 Å/Alq$_3$ 200 Å/LiF 5 Å/Al 1000 Å.

EXAMPLE 2-2

The organic photoelectric device was fabricated according to the same manner of Example 2-1, except that the organic compound (10) was used as a host instead of the organic compound (5) of Example 2-1. The organic photoelectric device has the following structure: ITO/NPD 300 Å/organic compound 10+Ir(piq)$_2$(acac) (5 wt %, 300 Å)/BAlq 50 Å/Alq$_3$ 200 Å/LiF 5 Å/Al 1000 Å.

COMPARATIVE EXAMPLE 1

The organic photoelectric device was fabricated according to the same manner of Example 2-1, except that 4,4-N,N-dicarbazolebiphenyl (CBP) having the following Formula 38 was used as a host instead of the organic compound (5) of Example 2-1. The organic photoelectric device has the following structure: ITO/NPD 300 Å/CBP+Ir(piq)$_2$(acac) (5 wt %, 300 Å)/BAlq 50 Å/Alq$_3$ 200 Å/LiF 5 Å/Al 1000 Å.

[Formula 38]

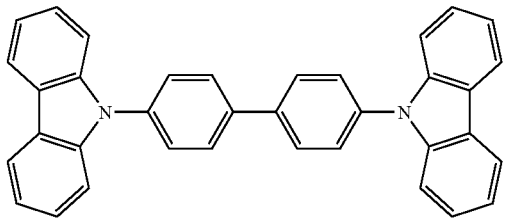

(Nuclear Magnetic Resonance and Mass Analysis of Organic Compound)

The organic compound having the above Formula 8 according to Example 1-1 was analyzed using 200 MHz H-NMR (H-Nuclear Magnetic Resonance) and LC-MS (Liquid Chromatograph-Mass Spectrometer).

$^1$H NMR (200 MHz, CDCl$_3$) δ 7.25-7.60 (m, 12H), 7.75 (m, 5H), 8.20 (d, 4H), 8.55 (d, 2H), 8.80 (d, 2H), 9.00 (d, 1H) ppm.

LC-MS calculation: $C_{40}H_{26}N_4$=562.7; measurement: m/z=563.2.

The organic compound having the above Formula 13 according to Example 1-2 was analyzed using 200 MHz H-NMR (H-Nuclear Magnetic Resonance) and LC-MS (Liquid Chromatograph-Mass Spectrometer).

$^1$H NMR (200 MHz, CDCl$_3$) δ 7.21-7.55 (m, 14H), 7.60-7.76 (m, 6H), 7.82-7.98 (m, 4H), 8.36 (s, 2H), 8.40-8.70 (m, 6H), 9.02 (d, 1H) ppm.

LC-MS calculation: $C_{52}H_{33}N_5$=727.9; measurement: m/z=728.3.

(Thermal Analysis Result of Organic Compound)

Glass transition temperature and thermal decomposition temperature of the organic compounds according to Example 1-1 and Example 1-2, and CBP of Comparative Example 1 were measured using differential scanning calorimetry (DSC) and thermogravimetric analysis (TGA). Thermal analysis measurement results are shown in the following Table 2.

TABLE 2

|  | Host material of emission layer | $T_g$ (° C.) | $T_d$ (° C.) |
|---|---|---|---|
| Example 1-1 | organic compound (5) | 127 | 487 |
| Example 1-2 | organic compound (10) | 124 | 474 |
| Comparative Example 1 | CBP | 110 | 392 |

Referring to Table 2, the organic compounds according to Example 1-1 and Example 1-2 show a glass transition temperature ($T_g$) of 120° C. or more and a thermal decomposition temperature ($T_d$) of 400° C. or more at DSC and TGA analyses, indicating that they have high thermal stability compared to the organic compound of Comparative Example 1.

(Performance Measurement of Organic Photoelectric Device)

Each organic photoelectric device according to Example 2-1, Example 2-2, and Comparative Example 1 was measured regarding luminous efficiency in accordance with a voltage as below.

1) Current Density According to a Voltage Change

Each organic photoelectric device according to Example 2-1, Example 2-2, and Comparative Example 1, was measured for a current value passing through the unit device using a current-voltage meter (Keithley 2400), while increasing the voltage from 0 V to 14 V. The results were calculated by dividing the measured current value by the area.

2) Luminance According to a Voltage Change

Each organic photoelectric device according to Example 2-1, Example 2-2, and Comparative Example 1 was measured for luminance by a luminance meter (Minolta Cs-1000A) while increasing the voltage from 0 V to 14 V.

3) Luminous Efficiency

Luminous efficiency was calculated by using the luminance, current density, and voltage measured from the above 1) and 2). The results are shown in Table 3.

TABLE 3

|  | Driving voltage (V) | Luminous efficiency (lm/W) | Color coordinate (x, y) |
|---|---|---|---|
| Example 2-1 | 9.0 | 2.9 | 0.68, 0.31 |
| Example 2-2 | 7.0 | 2.8 | 0.68, 0.32 |
| Comparative Example 1 | 9.3 | 2.5 | 0.68, 0.32 |

The organic photoelectric devices including Example 2-1 and Example 2-2 show a driving voltage of 9 V or less at a luminance of 500 nit, which may be more than 2 V less than the 9.3 V of Comparative Example 1. The organic photoelectric devices including Example 2-1 and Example 2-2 may show significantly improved luminous efficiency compared to that according to Comparative Example 1.

The organic compounds according to embodiments may have high thermal stability, a low driving voltage, and high luminous efficiency, indicating that they can improve the life-span of the organic photoelectric devices.

Embodiments may provide a phosphorescent light emitting material for an organic photoelectric device having thermal stability with a glass transition temperature ($T_g$) of about 120° C. or more and a thermal decomposition temperature ($T_d$) of about 400° C. or more, and being suitable for a high efficiency organic photoelectric device. The material may be used singularly, as a host material in combination with a dopant, etc. The material may include a symmetric or asymmetric bipolar organic compound including both a hole transporting unit and an electron transporting unit. An organic photoelectric device may be formed using the material. The material according to embodiments may be used as, e.g., a phosphorescent host material, to provide an organic photoelectric device having electrical stability, long lifetime, where the material is used to transport both holes and electrons.

In contrast, a host material that includes 4,4-N,N-dicarbazolebiphenyl (CBP), having a glass transition temperature of 110° C. or less and a thermal decomposition temperature of 400° C. or less, may have a thermal stability that is low and symmetry that is excessively high. Further, it may tend to crystallize and cause problems such as a short and a pixel defect according to results of thermal resistance tests of the devices. In addition, host materials including CBP may be materials in which the hole transporting property is greater than the electron transporting property. Thus, as the injected hole transportation is faster than the injected electron transportation, the excitons may be ineffectively formed in the emission layer. Therefore, the resultant device may have low luminous efficiency.

Example embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A material for an organic photoelectric device, the material comprising a compound represented by any one of the following Formulae 4 to 13, 16 to 19, 22, 25, 28, 31 to 34, and 37:

-continued
[Formula 4]
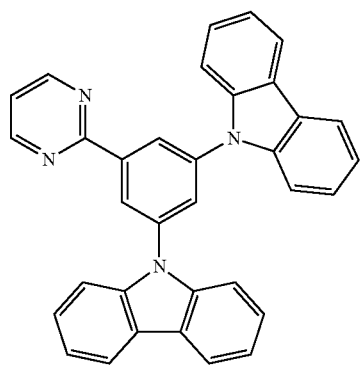
[Formula 8]
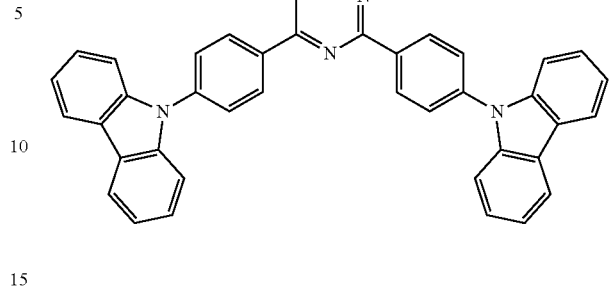
[Formula 5]
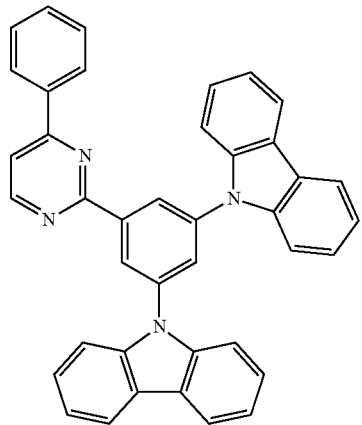
[Formula 9]
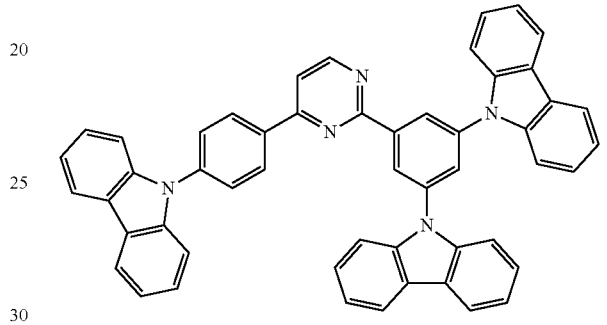
[Formula 10]
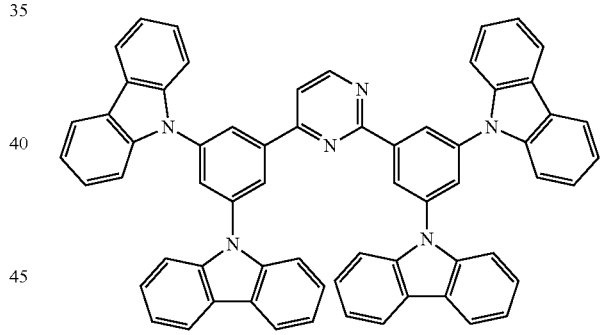
[Formula 6]
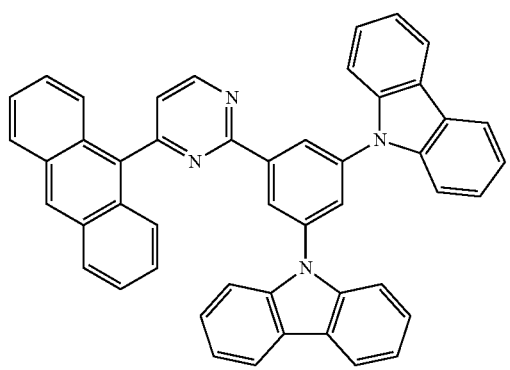
[Formula 7]
[Formula 11]
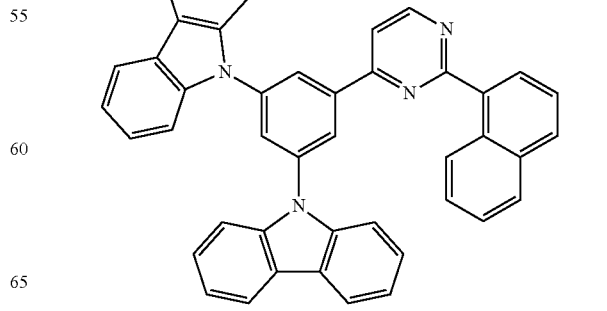

[Formula 12]
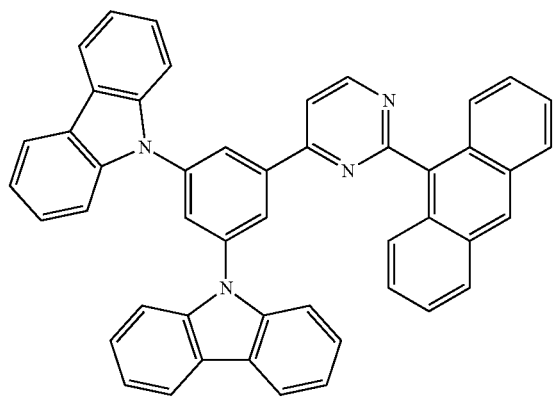
[Formula 13]
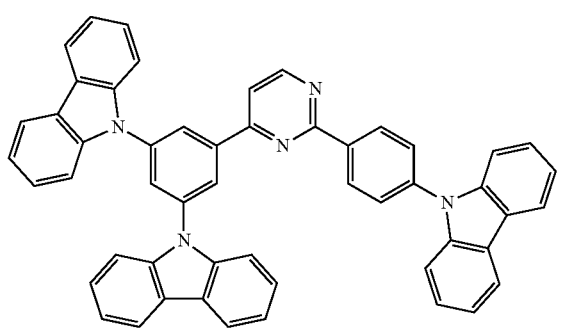
[Formula 16]
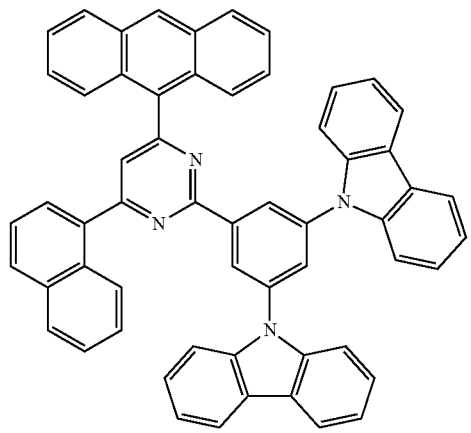
[Formula 17]
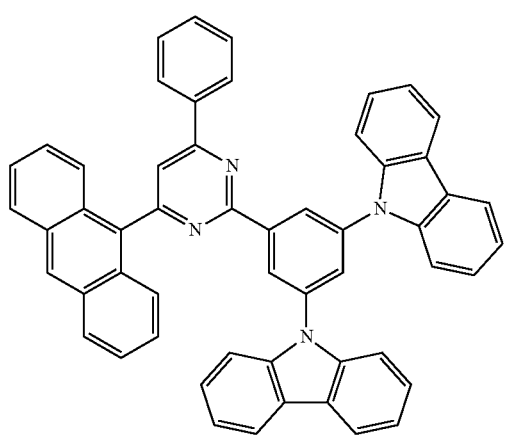
[Formula 18]
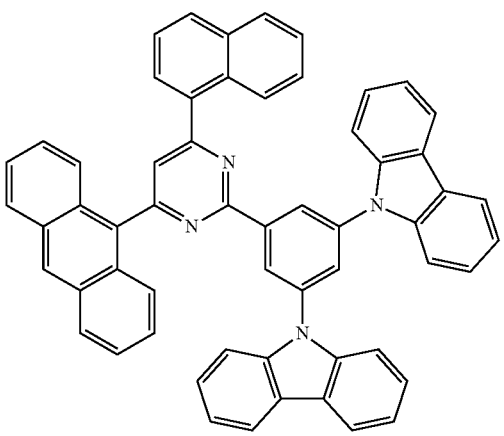
[Formula 19]
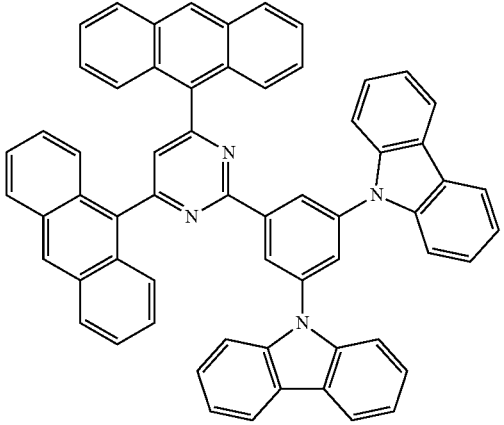
[Formula 22]
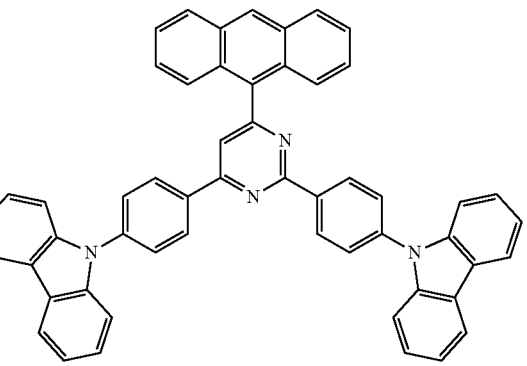

[Formula 25]
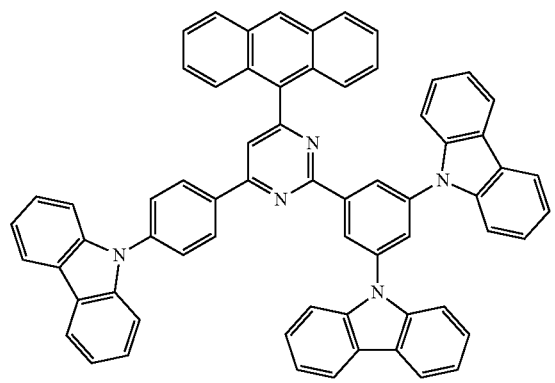
[Formula 32]
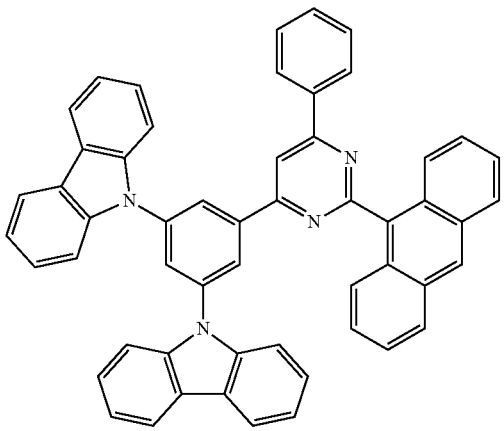
[Formula 28]
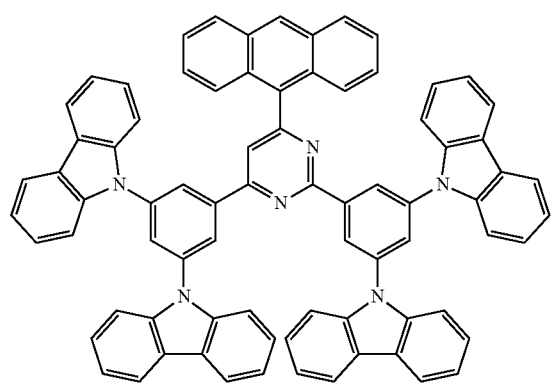
[Formula 33]
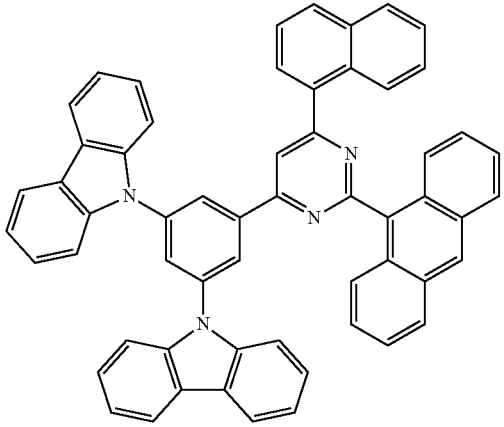
[Formula 31]
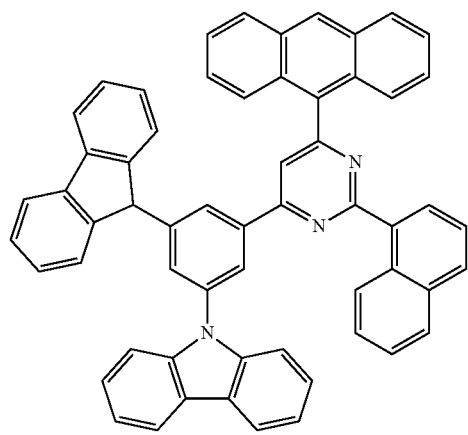
[Formula 34]
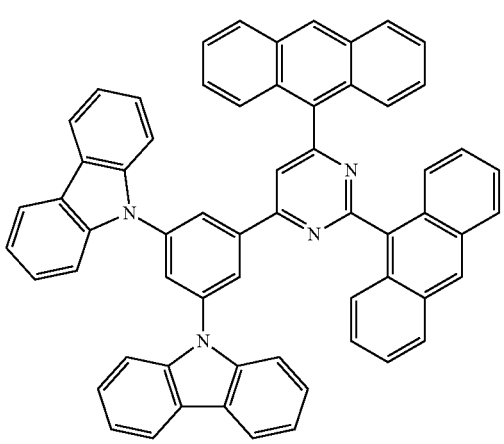

[Formula 37]
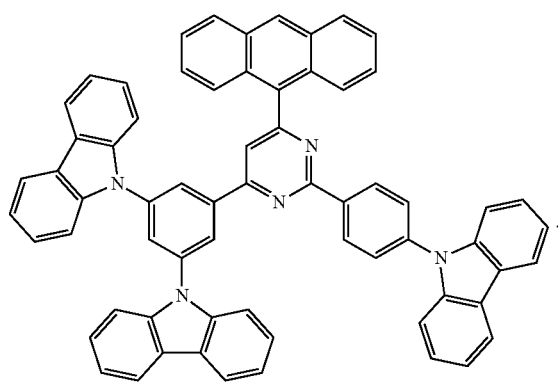
2. The material as claimed in claim 1, wherein the compound is represented by any one of the following Formulae 4 to 10:
[Formula 4]
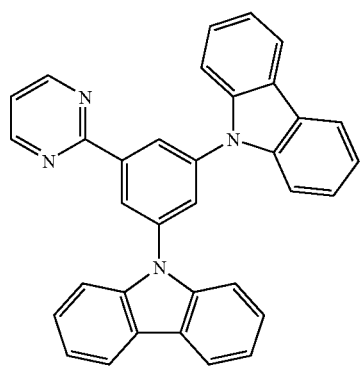
[Formula 5]
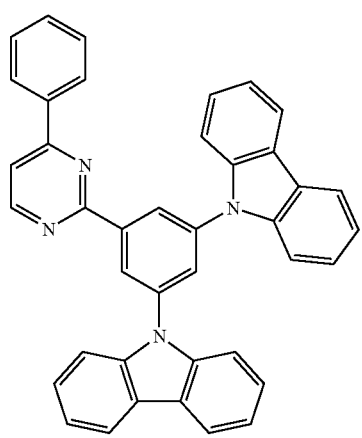
[Formula 6]
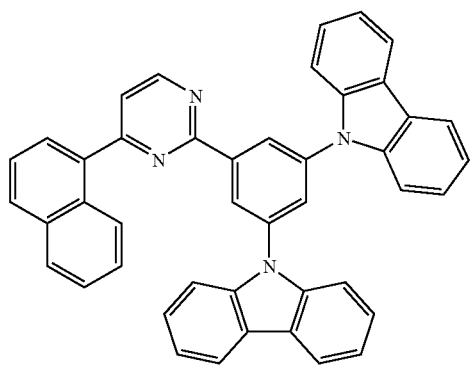
[Formula 7]
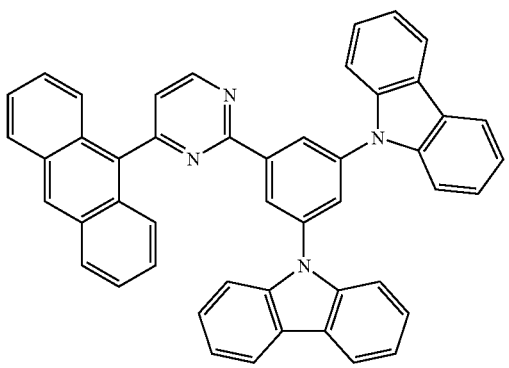
[Formula 8]
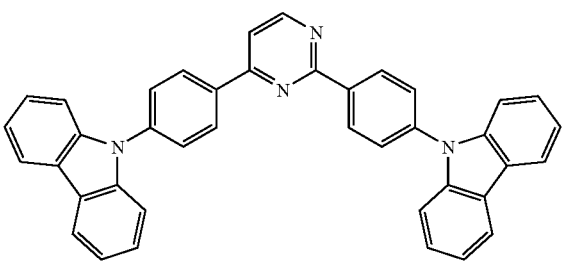
[Formula 9]
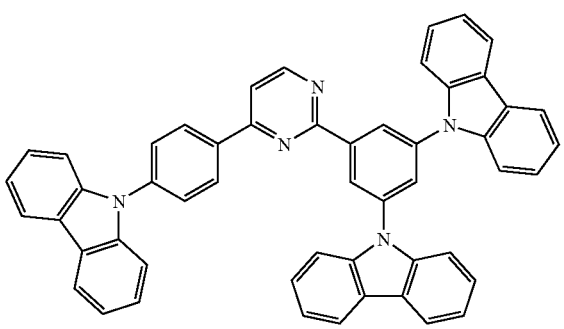

[Formula 10]
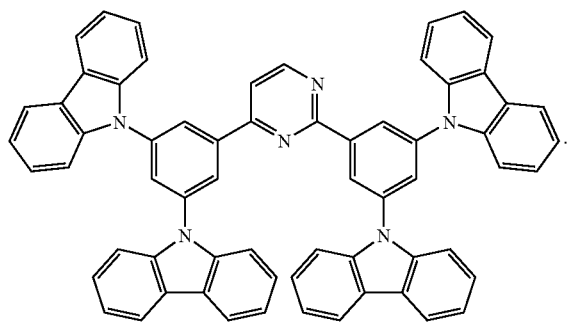
3. The material as claimed in claim 1, wherein the compound is represented by any one of the following Formulae 11 to 13, and 16:
[Formula 11]
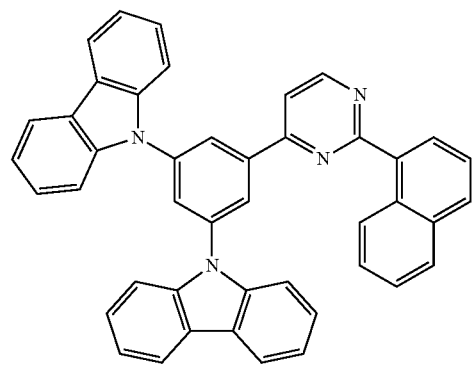
[Formula 12]
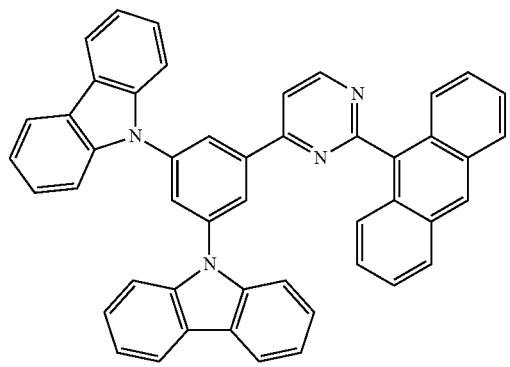
[Formula 13]
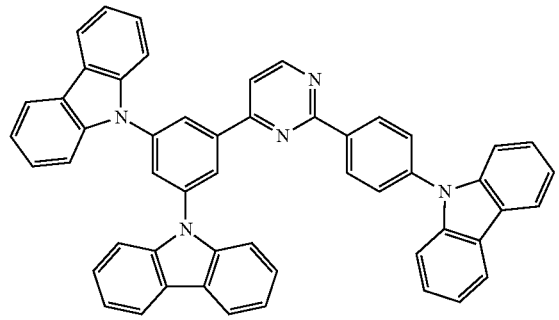
[Formula 16]
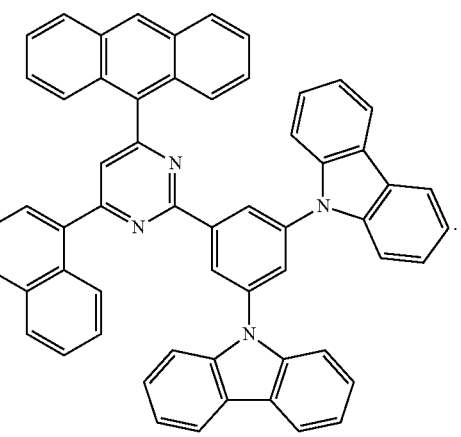
4. The material as claimed in claim 1, wherein the compound is represented by any one of the following Formulae 17 to 19, and 22:
[Formula 17]
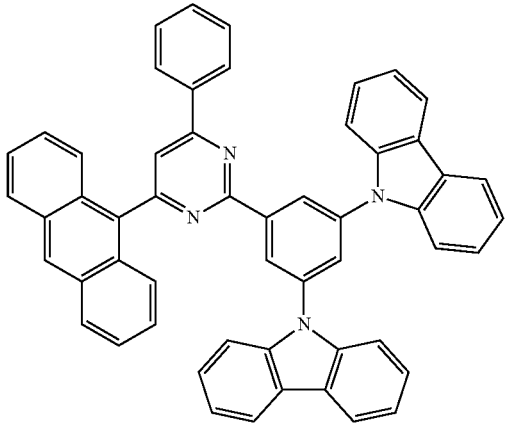
[Formula 18]
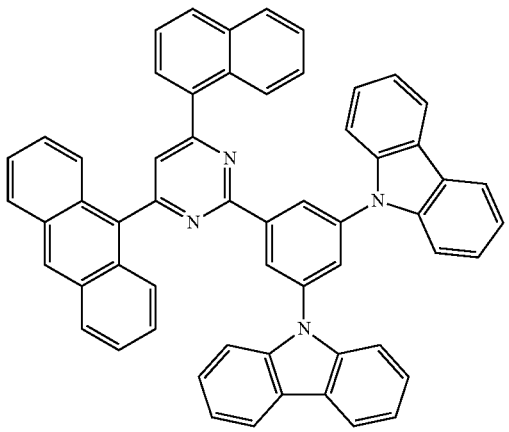

[Formula 19]
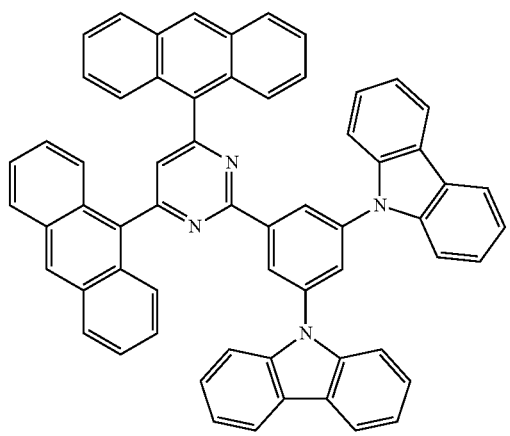
[Formula 28]
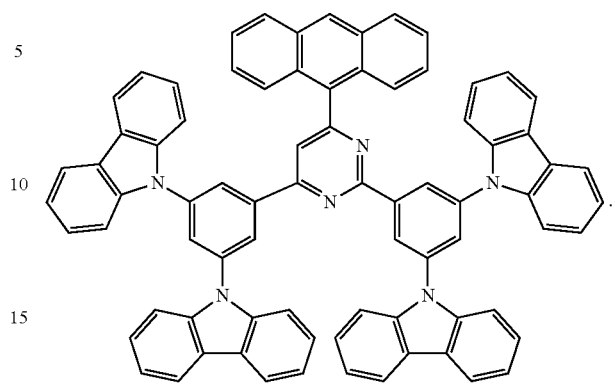
6. The material as claimed in claim 1, wherein the compound is represented by any one of the following Formulae 31 to 34:
[Formula 31]
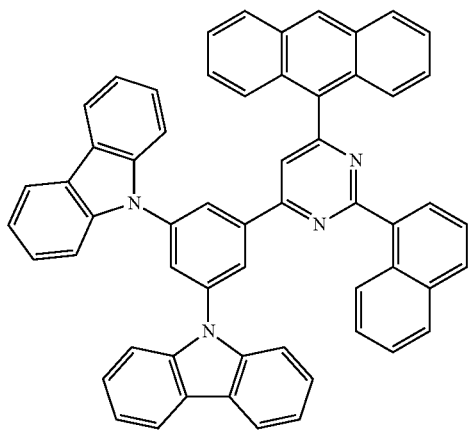
[Formula 22]
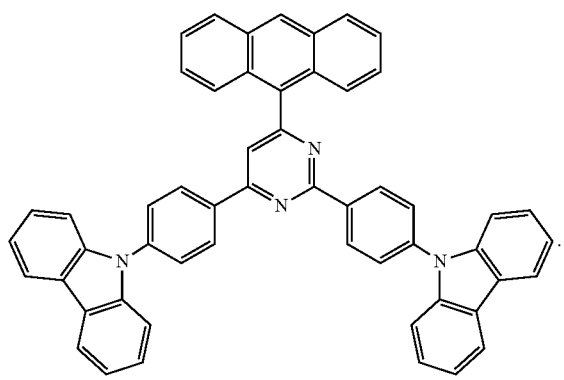
5. The material as claimed in claim 1, wherein the compound is represented by any one of the following Formulae 25 and 28:
[Formula 25]
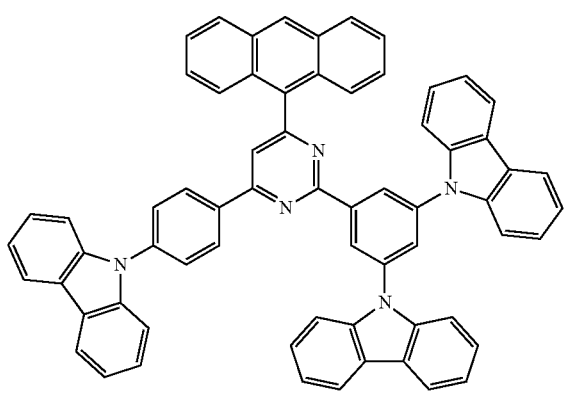
[Formula 32]
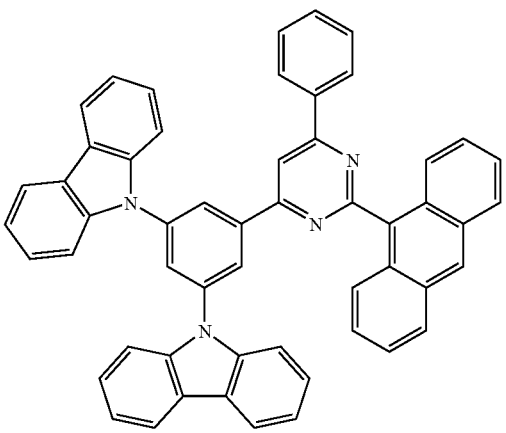

[Formula 33]

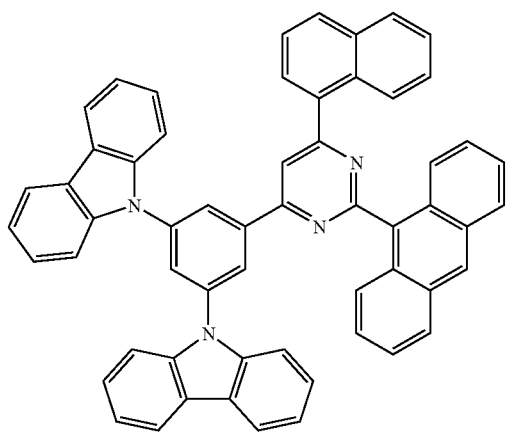

[Formula 34]

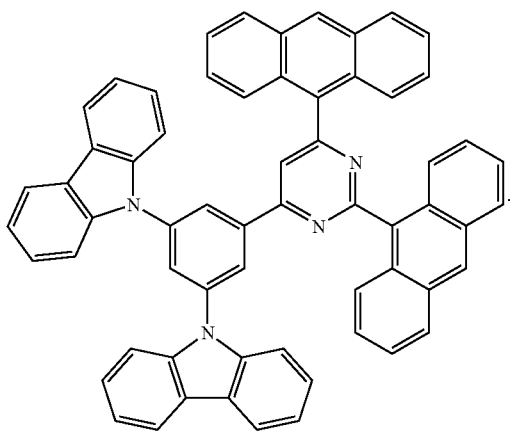

7. The material as claimed in claim 1, wherein the compound is represented by Formula 37:

[Formula 37]

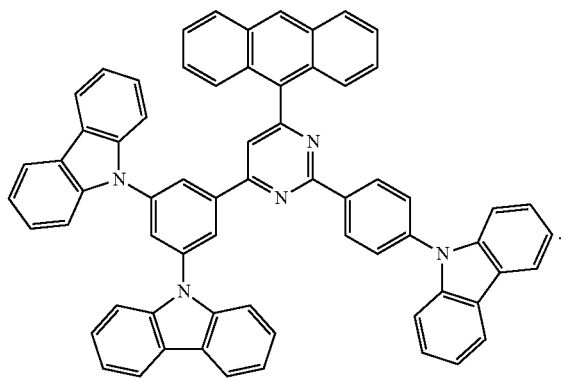

8. The material as claimed in claim 1, wherein the compound has a glass transition temperature of about 120° C. or more and has a thermal decomposition temperature of about 400° C. or more.

9. An organic photoelectric device, comprising:
an anode, a cathode, and an organic layer disposed between the anode and cathode,
wherein the organic layer includes the material as claimed in claim 1.

10. The organic photoelectric device as claimed in claim 9, wherein the organic layer is an electron transport layer (ETL), an electron injection layer (EIL), or a combination thereof.

11. The organic photoelectric device as claimed in claim 9, wherein the organic layer is an emission layer, a hole transport layer (HTL), a hole injection layer (HIL), an electron transport layer (ETL), an electron injection layer (EIL), or a combination thereof.

12. The organic photoelectric device as claimed in claim 9, wherein the organic layer is an emission layer.

13. The organic photoelectric device as claimed in claim 12, wherein the compound is a fluorescent blue dopant in the emission layer.

14. The organic photoelectric device as claimed in claim 12, wherein the compound is present as a phosphorescent or fluorescent host of the emission layer.

15. The organic photoelectric device as claimed in claim 14, further comprising a phosphorescent or fluorescent dopant combined with the host, the dopant being a red, green, blue, or white light emitting dopant.

* * * * *